United States Patent
Blouin et al.

(10) Patent No.: US 9,455,059 B2
(45) Date of Patent: Sep. 27, 2016

(54) PHENANTHRO [1,10,9,8-C,D,E,F,G]CARBAZOLE POLYMERS AND THEIR USE AS ORGANIC SEMICONDUCTORS

(75) Inventors: Nicolas Blouin, Southhampton (GB); William Mitchell, Chandler's Ford (GB); Changsheng Wang, Durham (GB); Steven Tierney, Southampton (GB)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 1121 days.

(21) Appl. No.: 13/389,906

(22) PCT Filed: Jul. 14, 2010

(86) PCT No.: PCT/EP2010/004262
§ 371 (c)(1),
(2), (4) Date: Feb. 10, 2012

(87) PCT Pub. No.: WO2011/018144
PCT Pub. Date: Feb. 17, 2011

(65) Prior Publication Data
US 2012/0138865 A1 Jun. 7, 2012

(30) Foreign Application Priority Data
Aug. 12, 2009 (EP) .................................... 09010387

(51) Int. Cl.
*H02B 1/00* (2006.01)
*C08G 61/00* (2006.01)
(Continued)

(52) U.S. Cl.
CPC ................. *H01B 1/12* (2013.01); *B82Y 10/00* (2013.01); *C07D 209/56* (2013.01); *C07D 417/14* (2013.01); *C08G 61/123* (2013.01); *C08G 61/124* (2013.01); *C08G 61/126* (2013.01); *C08L 65/00* (2013.01); *C09K 11/06* (2013.01); *H01L 51/0036* (2013.01); *H05B 33/14* (2013.01); *C08G 2261/3223* (2013.01);
(Continued)

(58) Field of Classification Search
CPC .......... H01B 1/00; H01B 1/12; H01B 1/121; C07D 209/56; C08G 61/12; H01L 511/00; H01L 511/0042
See application file for complete search history.

(56) References Cited

U.S. PATENT DOCUMENTS

2005/0014926 A1 1/2005 Towns et al.
2010/0006154 A1 1/2010 Kitazawa et al.

FOREIGN PATENT DOCUMENTS

| EP | 2 072 557 | 6/2009 |
| JP | 2009 59839 | 3/2009 |
| WO | WO-00 53656 | 9/2000 |

OTHER PUBLICATIONS

Chalmers, John M. Meier, Robert J.. (2008). Comprehensive Analytical Chemistry, vol. 53—Molecular Characterization and Analysis of Polymers—2.2 Polymer: Definitions. Elsevier. p. 15.*

(Continued)

*Primary Examiner* — Mark Kopec
(74) *Attorney, Agent, or Firm* — Millen White Zelano and Branigan, PC; Csaba Henter; Anthony Zelano

(57) ABSTRACT

The invention relates to novel phenanthro[1,10,9,8-c,d,e,f, g]carbazole polymers, methods and materials for their preparation, their use as semiconductors in organic electronic (OE) devices, and to OE devices comprising these polymers.

21 Claims, 1 Drawing Sheet

(51) Int. Cl.
| | |
|---|---|
| *H01B 1/12* | (2006.01) |
| *B82Y 10/00* | (2011.01) |
| *C07D 209/56* | (2006.01) |
| *C07D 417/14* | (2006.01) |
| *C08G 61/12* | (2006.01) |
| *C08L 65/00* | (2006.01) |
| *C09K 11/06* | (2006.01) |
| *H01L 51/00* | (2006.01) |
| *H05B 33/14* | (2006.01) |
| *H01L 51/42* | (2006.01) |

(52) U.S. Cl.
CPC ........... *C08G2261/3229* (2013.01); *C08G 2261/3241* (2013.01); *C08G 2261/411* (2013.01); *C08G 2261/51* (2013.01); *C08G 2261/596* (2013.01); *C08G 2261/91* (2013.01); *C08G 2261/92* (2013.01); *C09K 2211/1466* (2013.01); *C09K 2211/1483* (2013.01); *H01L 51/0047* (2013.01); *H01L 51/4253* (2013.01); *Y02E 10/549* (2013.01); *Y02P 70/521* (2015.11)

(56) References Cited

OTHER PUBLICATIONS

Bao, Z. et al., "Exploration of the stille coupling reaction for the synthese of functional polymers," J. Am. Chem. Soc., 1995, vol. 117, pp. 12426-12435.

Blouin, N. et al., "A low-bandgap poly(2,7-Carbazole) derivative for use in high performance solar cells," Adv. Mater., 2007, vol. 19, pp. 2295-2300.

Blouin, N. et al., "Poly(2,7-carbazole)s: Structure—Property Relationships," Accounts of Chemical Research, Sep. 2008, vol. 41, No. 9, pp. 1110-1119.

Blouin, N. et al., "Toward a rational design of poly(2,7-carbazole) derivatives for solar cells," J. Am. Chem. Soc., 2008, vol. 130, pp. 732-742.

Boudreault, P. et al., "Poly(2,7-carbazole)s and Related Polymers," Adv Polym Sci, 2008, vol. 212, pp. 99-124.

Database WPI Week 200927, XP002605280, 2009.

Dennler, G. et al., "Polymer-fullerene bulk-heterojunction solar cells," Adv. Mater. 2009, vol. 21, pp. 1323-1338.

Grazulevicius, J. V. et al., "Carbazole-containing polymers: synthesis, properties and applications," Prog. Polym. Sci., 2003, vol. 28, pp. 1297-1353.

International Search Report for PCT/EP2010/004262 dated Jul. 13, 2011.

Jiang, W. et al., "Heteroatom-annulated perylenes: Practical synthesis, photophysical properties, and solid-state packing arrangement," J. Org. Chem., 2008, vol. 73, pp. 7369-7372.

Li, Y. et al., "Bis-N-Annulated Quaterrylene: An approach to processable grapheme nanoribbons," J. Chem. Phys., 1985, vol. 83, No. 1316, pp. 1385-1387.

Looker, J. J., "Mononitration of perylene. Preparation and Structure Proof of the 1 and 3 Isomers," J. Org. Chem., 1972, vol. 37, No. 21, pp. 3379-3381.

Marzoni, G. et al., "$N^1$-Alkylation of Dihydrolysergic Acid," Communications, Jul. 1987, pp. 651-653.

Mitsui Chemicals Inc., "Organic transistor," Espacenet, Publication Date: Mar. 19, 2009; English Abstract of JP-2009 059839.

Morin, J. et al., "Polycarbazoles: 25 Years of Progress," Macromol. Rapid Commun., 2005, vol. 26, pp. 761-778.

Morin, J. et al., "Syntheses of conjugated polymers derived from n-alkyl-2,7-carbazoles," Macromolecules, 2001, vol. 34, pp. 4680-4682.

Park, S. H. et al., "Bulk heterojunction solar cells with internal quantum efficiency approaching 100%," Nature Photonics, May 2009, vol. 3, pp. 297-303.

Scherf, U. et al., "Semiconducting polyfluorenes—towards reliable structure-property relationships," Adv. Mater., 2002, vol. 14, No. 7, pp. 477-487.

Schluter, A. D. et al., "The Tenth Anniversary of Suzuki Polycondensation (SPC)," Journal of Polymer Science: Part A: Polymer Chemistry, 2001, vol. 39, pp. 1533-1556.

Sirringhaus, H. et al., "Two-dimensional charge transport in self-organized, high-mobility conjugated polymers," Nature, Oct. 14, 1999, vol. 401, pp. 685-688.

Sun, Y. et al., "High-performance transistor based on individual single-crystalline micrometer wire of perylo [1,12-b,c,d]thiophene," J. Am. Chem. Soc., 2007, vol. 129, pp. 1882-1883.

Van Mullekom, H. A. M. et al., "Developments in the chemistry and band gap engineering of donor-acceptor substituted conjugated polymers," Materials Science and Engineering, 2001, vol. 32, pp. 1-40.

Yamamoto, T., "Synthesis of π-conjugated polymers bearing electronic and optical functionalities by organometallic polycondensations. Chemical Properties and applications of the π-conjugated polymers," Synlett, 2003, No. 4, pp. 425-450.

Search Report related to corresponding Taiwanese Patent Application No. 099126799, dated Oct. 13, 2014.

\* cited by examiner

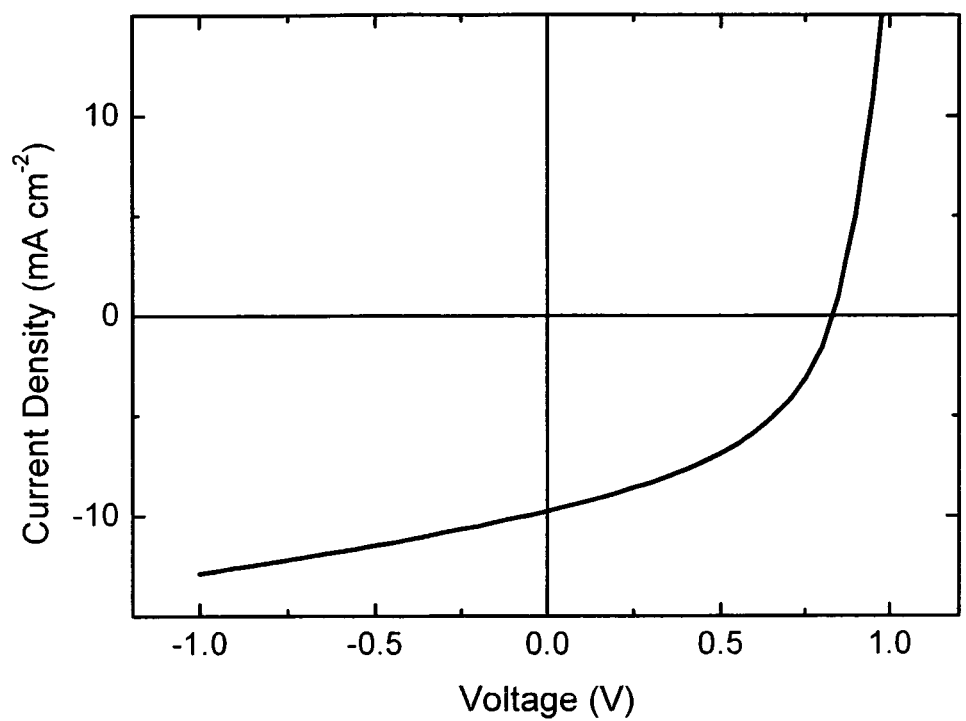

PHENANTHRO[1,10,9,8-C,D,E,F,G]CARBAZOLE POLYMERS AND THEIR USE AS ORGANIC SEMICONDUCTORS

FIELD OF THE INVENTION

The invention relates to novel phenanthro[1,10,9,8-c,d,e,f,g]carbazole polymers, methods and materials for their preparation, their use as semiconductors in organic electronic (OE) devices, and to OE devices comprising these polymers.

BACKGROUND OF THE INVENTION

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), photodetectors, organic photovoltaic (OPV) cells, sensors, memory elements and logic circuits to name just a few. The organic semiconducting materials are typically present in the electronic device in the form of a thin layer, for example less than 1 micron thick.

The performance of OFET devices is principally based upon the charge carrier mobility of the semiconducting material and the current on/off ratio, so the ideal semiconductor should have a low conductivity in the off state, combined with a high charge carrier mobility ($>1\times10^{-3}$ cm$^2$ V$^{-1}$ s$^{-1}$). In addition, it is important that the semiconducting material is relatively stable to oxidation i.e. it has a high ionisation potential, as oxidation leads to reduced device performance. Further requirements for the semiconducting material are a good processability, especially for large-scale production of thin layers and desired patterns, and high stability, film uniformity and integrity of the organic semiconductor layer.

Nitrogen containing small molecules, oligomers and polymers have demonstrated interesting hole transport properties.[1-5] Various materials have been developed to take advantage of this physical property in organic light emitting devices (OLED), in organic field-effect transistors (OFET) and organic photovoltaic cells (OPV). However, most of those materials show poor solubility or poor structural organization in the solid state.[1-5] Furthermore, these materials have generally required complex synthetic routes to yield the final material.

Therefore, there is still a need for OSC materials that are easy to synthesize, show good structural organization and film-forming properties, exhibit good electronic properties, especially a high charge carrier mobility, good processibilty, especially a high solubility in organic solvents, and high stability in air. For use in OFETs there is also a need for OSC materials that allow improved charge injection into the semiconducting layer from the source-drain electrodes. For use in OPV cells, there is a need for OSC materials having a low band-gap, which enable improved light harvesting by the photoactive layer and can lead to higher cell efficiencies.

It was an aim of the present invention to provide compounds for use as organic semiconducting materials that do not have the drawbacks of prior art materials as described above, are easy to synthesize, and do especially show good processibility, high stability, good solubility in organic solvents, high charge carrier mobility, and a low band-gap. Another aim of the invention was to extend the pool of organic semiconducitng materials available to the expert. Other aims of the present invention are immediately evident to the expert from the following detailed description.

The inventors of the present invention have found that these aims can be achieved by providing materials as described hereinafter. These materials are based on polymers comprising one or more phenanthro[1,10,9,8-c,d,e,f,g]carbazole units.

It was found that these polymers are suitable for use as OSC materials in electronic devices, especially in OFETs and OPV cells, and as charge transport layer or interlayer material in polymer light emitting diodes (PLEDs), as they have good processibility and solubility, and at the same time show a high charge carrier mobility, a low band-gap and a high oxidative stability.

In particular it was found that polymers having one or more phenanthro[1,10,9,8-c,d,e,f,g]carbazole units have similar hole transport and photovoltaic properties compared to polycarbazoles, but with improved pi-pi stacking and solid state organization.

Initially reported in 2001[6] poly(2,7-carbazole)s have been suggested as materials for organic electronic, particularly for OPV with power conversion efficiency <6%.[7-9] Similar to this carbazole core, the synthesis of phenanthro[1,10,9,8-c,d,e,f,g]carbazole core has been recently reported.[10-12] The phenanthro[1,10,9,8-c,d,e,f,g]carbazole and other similar derivatives exhibit good pi-pi stacking in the solid state.[11] For example in perylo[1,12-b,c,d]thiophene, which is an isoelectronic analogue, the intermolecular packing results in a high hole mobility (0.05 cm$^2$·V$^{-1}$·s$^{-1}$) in thin-film OFETs and significantly higher mobility (0.8 cm$^2$·V$^{-1}$·s$^{-1}$) in single-crystal wire OFETs.[13] However, there have been no reports that the phenanthro[1,10,9,8-c,d,e,f,g]carbazole unit has been successfully integrated into a polymeric structure. The low solubility of the initially reported phenanthro[1,10,9,8-c,d,e,f,g]carbazole structure limits its extension into a polymeric structure.[11,12] Furthermore, the inclusion of the phenanthro[1,10,9,8-c,d,e,f,g]carbazole ladder-structure, namely the bis-N-annulated quaterrylene,[10] into a polymeric structure would also result in low solubility due to the highly extended aromatic unit in the polymer backbone that would lead to aggregation.

SUMMARY OF THE INVENTION

The invention relates to conjugated polymers comprising one or more identical or different repeating units of formula I (phenanthro[1,10,9,8-c,d,e,f,g]carbazole and its derivatives):

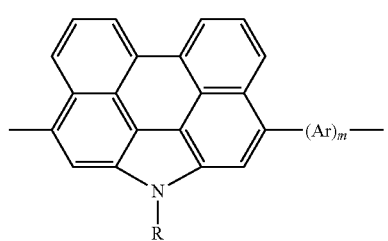

wherein
R is on each occurrence identically or differently H, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR$^0$=CR$^{00}$— or —C≡C— and in which one or more H atoms are optionally replaced by F, Cl, Br, I or CN, or R is an aryl, heteroaryl, aryloxy or heteroaryloxy group having 2 to 40 C atoms that is unsubstituted or substituted by one or more non-aromatic groups $R^1$, $R^0$ and $R^{00}$ are independently of each other H or an optionally substituted carbyl or hydrocarbyl group optionally comprising one or more hetero atoms, Ar is on each occurrence identically or differently an optionally substituted aryl or heteroaryl group, —$CY^1$=$CY^2$— or —C≡C—, $Y^1$ and $Y^2$ are independently of each other H, F, Cl or CN, $R^1$ is on each occurrence identically or differently H, halogen, —CN, —NC, —NCO, —NCS, —OCN, —SCN, —C(=O)$NR^0R^{00}$, —C(=O)$X^0$, —C(=O)$R^0$, —$NH_2$, —$NR^0R^{00}$, —SH, —$SR^0$, —$SO_3H$, —$SO_2R^0$, —OH, —$NO_2$, —$CF_3$, —$SF_5$, optionally substituted silyl, carbyl or hydrocarbyl with 1 to 40 C atoms that is optionally substituted and optionally comprises one or more hetero atoms, or P-Sp-, P is a polymerisable group, Sp is a spacer group or a single bond, $X^0$ is halogen, and m is on each occurrence identically or differently 0, 1, 2 or 3, and the benzene rings are optionally substituted with one or more groups R.

The invention further relates to a mixture or blend comprising one or more polymers according to the present invention and one or more compounds or polymers, preferably selected from compounds and polymers having semiconducting, charge transport, hole/electron transport, hole/electron blocking, electrically conducting, photoconducting or light emitting properties.

The invention further relates to a formulation comprising one or more polymers or blends according to the present invention and one or more solvents, preferably selected from organic solvents.

The invention further relates to the use of polymers, blends and formulations according to the present invention as charge transport, semiconducting, electrically conducting, photoconducting or light emitting material in optical, electrooptical, electronic, electroluminescent or photoluminescent components or devices.

The invention further relates to a charge transport, semiconducting, electrically conducting, photoconducting or light emitting material or component comprising one or more polymers, polymer blends of formulations according to the present invention.

The invention further relates to an optical, electrooptical or electronic component or device comprising one or more polymers, mixtures, blends, formulations, components or materials according to the present invention.

The optical, electrooptical, electronic electroluminescent and photoluminescent components or devices include, without limitation, organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

BRIEF DESCRIPTION OF THE DRAWINGS

FIG. 1 shows the OPV device characteristics of an OPV device in accordance with Example 6 the present invention.

DETAILED DESCRIPTION OF THE INVENTION

This invention relates to a novel class of polymers and copolymers based on the phenanthro[1,10,9,8-c,d,e,f,g]carbazole unit, preferably containing a solubilizing group R, as shown in formula I. These polymers are synthesized in a regioregular and regioselective fashion via chemical polymerization.

The polymers of the present invention are easy to synthesize and exhibit several advantageous properties, like a low bandgap, a high charge carrier mobility, a high solubility in organic solvents, a good processability for the device manufacture process, a high oxidative stability and a long lifetime in electronic devices. In addition, they show the following advantageous properties:

i) The addition of two alkyl or alkylated aryl or alkoxylated aryl groups or a mix of both, especially in the position of group R in formula I, is expected to help dissolving the polymeric material in common organic solvents allowing the material to be easily solution processed. The addition of the alkyl or alkylated aryl or alkoxylated aryl side groups should also promote the material to exhibit better pi-pi stacking and thus form highly microstructurally organized films after deposition from solution.[1,14,15]

ii) The phenanthro[1,10,9,8-c,d,e,f,g]carbazole and other similar derivatives exhibit a good pi-pi stacking in the solid state.[11] Such packing can result in high hole mobility (0.8 $cm^2 \cdot V^{-1} \cdot s^{-1}$) in OFETs.[13] This extended aromatic unit and its high intermolecular order will result in better pi-pi stacking of the resulting polymer in the solid state compared to the poly(2,7-carbazole)s and similar polymers, leading to better hole transport.

iii) The addition of reactive functionality onto specific positions on the phenanthro[1,10,9,8-c,d,e,f,g]carbazole core will enable the preparation of regioregular chemically polymerized homopolymers and copolymers. Such polymers can be obtained using Yamamoto,[16,17] Suzuki[18] or Stille[19] coupling polymerization methods. By these preparative methods, the regioregular polymer will have higher structural order in the solid state compared to regioirregular materials synthesized using a non-selective polymerization method. This will lead to a polymer with higher charge carrier mobility for application in OFET and OPV devices.

iv) It has been shown that the optical properties of conjugated polymers can generally be modulated by the generation of a donor-acceptor copolymer structure.[20] As an electron rich unit, the phenanthro[1,10,9,8-c,d,e,f,g]carbazole unit is a good donor comonomer, which is ideal for such donor-acceptor polymer structures. This would lead to low band-gap polymers for OPV applications or green, yellow and red fluorescing polymers for OLED applications. Furthermore, the HOMO and LUMO energy levels of the resulting polymers could be fine-tuned to the application requirements.[21]

v) The HOMO energy level of the poly-2,7-(phenanthro[1,10,9,8-c,d,e,f,g]carbazole)s could be expected to be similar to those of polycarbazoles and polyindolo[3,2-b]carbazoles (−5.3 to −5.5 eV),[1,2,4] which should lead to air stable polymers. Furthermore, a higher open circuit potential ($V_{oc}$) could be obtained in an OPV bulk-heterojunction device versus a device containing poly(3-hexylthiophene) (P3HT).

vi) In phenanthro[1,10,9,8-c,d,e,f,g]carbazole containing donor-acceptor polymers, the inclusion of additional electron-donating comonomers will yield a broad UV-Vis absorption spectrum with high absorption coefficient, thus leading to greater photon harvesting in an OPV bulk-heterojunction device. The inclusion of the extended aromatic unit, phenanthro[1,10,9,8-c,d,e,f,g]carbazole, into appropriately designed donor-acceptor polymers can provide a unique advantage over prior art materials that exhibit a low absorption coefficient in some regions between 300-800 nm.[10-12]

The term "polymer" or "polymeric compound" generally means a molecule of high relative molecular mass, the structure of which essentially comprises the multiple repetition of units derived, actually or conceptually, from molecules of low relative molecular mass (PAC, 1996, 68, 2291). The term "oligomer" generally means a molecule of intermediate relative molecular mass, the structure of which essentially comprises a small plurality of units derived, actually or conceptually, from molecules of lower relative molecular mass (PAC, 1996, 68, 2291). In a preferred sense according to the present invention a polymer means a compound having >1, preferably ≥5 repeating units, and an oligomer means a compound with >1 and <10, preferably <5, repeating units.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (PAC, 1996, 68, 2291).

The term "leaving group" means an atom or group (charged or uncharged) that becomes detached from an atom in what is considered to be the residual or main part of the molecule taking part in a specified reaction (see also PAC, 1994, 66, 1134).

The term "conjugated" means a compound containing mainly C atoms with $sp^2$-hybridisation (or optionally also sp-hybridisation), which may also be replaced by hetero atoms. In the simplest case this is for example a compound with alternating C—C single and double (or triple) bonds, but does also include compounds with units like 1,3-phenylene. "Mainly" means in this connection that a compound with naturally (spontaneously) occurring defects, which may lead to interruption of the conjugation, is still regarded as a conjugated compound.

Unless stated otherwise, the molecular weight is given as the number average molecular weight $M_n$ or weight average molecular weight $M_w$, which is determined by gel permeation chromatography (GPC) against polystyrene standards. The degree of polymerization (n) means the number average degree of polymerization, given as $n=M_n/M_U$, wherein $M_U$ is the molecular weight of the single repeating unit.

The term "carbyl group" as used above and below denotes any monovalent or multivalent organic radical moiety which comprises at least one carbon atom either without any non-carbon atoms (like for example —C≡C—), or optionally combined with at least one non-carbon atom such as N, O, S, P, Si, As, Te or Ge (for example carbonyl etc.). The term "hydrocarbyl group" denotes a carbyl group that does additionally contain one or more H atoms and optionally contains one or more hetero atoms like for example N, O, S, P, Si, Se, As, Te or Ge.

A carbyl or hydrocarbyl group comprising a chain of 3 or more C atoms may also be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1$-$C_{40}$ carbyl or hydrocarbyl group is acyclic, the group may be straight-chain or branched. The $C_{10}$-$C_{40}$ carbyl or hydrocarbyl group includes for example: a $C_1$-$C_{40}$ alkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ alkyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_2$-$C_{20}$ alkenyl group, a $C_2$-$C_{20}$ alkynyl group, a $C_3$-$C_{20}$ alkyl group, a $C_4$-$C_{20}$ alkyldienyl group, a $C_6$-$C_{12}$ aryl group and a $C_4$-$C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

Aryl and heteroaryl preferably denote a mono-, bi- or tricyclic aromatic or heteroaromatic group with up to 25 C atoms that may also comprise condensed rings and is optionally substituted with one or more groups L as defined above.

Very preferred substituents L are selected from halogen, most preferably F, or alkyl, alkoxy, oxaalkyl, thioalkyl, fluoroalkyl and fluoroalkoxy with 1 to 12 C atoms or alkenyl, alkynyl with 2 to 12 C atoms.

Especially preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, pyridine, preferably 2- or 3-pyridine, pyrimidine, thiophene preferably 2-thiophene, selenophene, preferably 2-selenophene, thieno[3,2-b]thiophene, thiazole, thiadiazole, oxazole and oxadiazole, especially preferably thiophene-2-yl, 5-substituted thiophene-2-yl or pyridine-3-yl, all of which can be unsubstituted, mono- or polysubstituted with L as defined above.

An alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

An alkenyl group, wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_{7-6}$-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example. Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one by —CO—, these radicals are preferably neighboured. Accordingly these radicals together form a carbonyloxy group —CO—O— or an oxycarbonyl group —O—CO—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —COO— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e where one $CH_2$ group is replaced by —S—, is preferably straight-chain thiomethyl (—$SCH_3$), 1-thioethyl (—$SCH_2CH_3$), 1-thiopropyl (=$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably straight-chain perfluoroalkyl wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

The above-mentioned alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methyl heptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In another preferred embodiment of the present invention, R is selected from primary, secondary or tertiary alkyl or alkoxy with 1 to 30 C atoms, wherein one or more H atoms are optionally replaced by F, or aryl, alkylated aryl or alkoxy aryl with 4 to 40 C atoms. Especially preferred groups R are selected from the group consisting of the following formulae

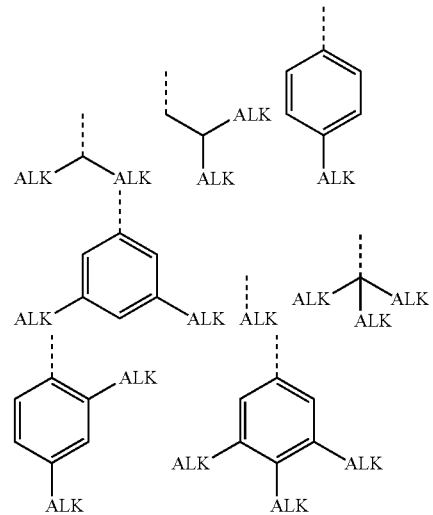

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the N-atom of the phenanthrocarbazole core in formula I. Especially preferred among these groups are those wherein all ALK subgroups are identical.

—CY$^1$=CY$^2$— is preferably —CH=CH—, —CF=CF— or —CH=C(CN)—.

Halogen is F, Cl, Br or I, preferably F, Cl or Br.

The polymers may also be substituted with a polymerisable or reactive group, which is optionally protected during the process of forming the polymer. Particular preferred polymers of this type are those of formula I wherein R$^1$ denotes P-Sp. These polymers are particularly useful as semiconductors or charge transport materials, as they can be crosslinked via the groups P, for example by polymerisation in situ, during or after processing the polymer into a thin film for a semiconductor component, to yield crosslinked polymer films with high charge carrier mobility and high thermal, mechanical and chemical stability.

Preferably the polymerisable or reactive group P is selected from $CH_2$=CW$^1$—CO—O—, $CH_2$=CW$^1$—CO—,

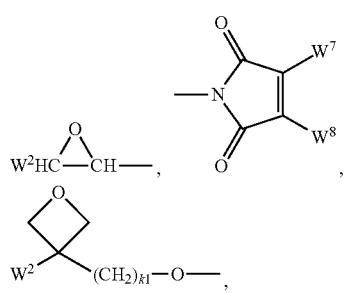

$CH_2$=CW$^2$—(O)$_{k1}$—, CW$^1$=CH—CO—(O)$_{k3}$—, CW$^1$=CH—CO—NH—, $CH_2$=CW$^1$—CO—NH—, $CH_3$—CH=CH—O—, $(CH_2$=CH)$_2$CH—OCO—, $(CH_2$=CH—$CH_2)_2$CH—O—CO—, $(CH_2$=CH)$_2$CH—O—, $(CH_2$=CH—$CH_2)_2$N—, $(CH_2$=CH—$CH_2)_2$N—CO—, HO—CW$^2$W$^3$—, HS—CW$^2$W$^3$—, HW$^2$N—, HO—CW$^2$W$^3$—NH—, $CH_2$=CH—(CO—O)$_{k1}$-Phe-(O)$_{k2}$—, $CH_2$=CH—(CO)$_{k1}$-Phe-(O)$_{k2}$—, Phe-CH=CH—, HOOC—, OCN—, and W$^4$W$^5$W$^6$Si—, with W$^1$ being H, F, Cl, CN, CF$_3$, phenyl or alkyl with 1 to 5 C-atoms, in particular H, Cl or CH$_3$, W$^2$ and W$^3$ being independently of each other H or alkyl with 1 to 5 C-atoms, in particular H, methyl, ethyl or n-propyl, W$^4$, W$^5$ and W$^6$ being independently of each other Cl, oxaalkyl or oxacarbonylalkyl with 1 to 5 C-atoms, W$^7$ and W$^8$ being independently of each other H, Cl or alkyl with 1 to 5 C-atoms, Phe being 1,4-phenylene that is optionally substituted by one or more groups L as defined above, $k_1$, $k_2$ and $k_3$ being independently of each other 0 or 1, $k_3$ preferably being 1, and $k_4$ being an integer from 1 to 10.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are $CH_2$=CH—CO—O—, $CH_2$=C(CH$_3$)—CO—O—, $CH_2$=CF—CO—O—, $CH_2$=CH—O—, $(CH_2$=CH)$_2$CH—O—CO—, $(CH_2$=CH)$_2$CH—O—,

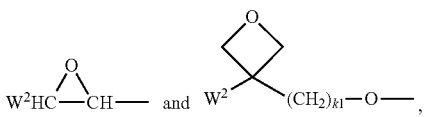

or protected derivatives thereof. Further preferred groups P are selected from the group consisting of vinyloxy, acrylate, methacrylate, fluoroacrylate, chloracrylate, oxetan and epoxy groups, very preferably an acrylate or methacrylate group.

Polymerisation of group P can be carried out according to methods that are known to the ordinary expert and described in the literature, for example in D. J. Broer; G. Challa; G. N. Mol, *Macromol. Chem.*, 1991, 192, 59.

The term "spacer group" is known in prior art and suitable spacer groups Sp are known to the ordinary expert (see e.g. Pure Appl. Chem. 73(5), 888 (2001). The spacer group Sp is preferably of formula Sp'-X', such that P-Sp- is P-Sp'-X'—, wherein Sp' is alkylene with up to 30 C atoms which is unsubstituted or mono- or polysubstituted by F, Cl, Br, I or CN, it being also possible for one or more non-adjacent $CH_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, X' is —O—, —S—, —CO—, —COO—, —OCO—, —O—COO—, —CO—NR$^0$—, —NR$^0$—CO—, —NR$^0$—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond, R$^0$ and R$^{00}$ are independently of each other H or alkyl with 1 to 12 C— atoms, and Y$^1$ and Y$^2$ are independently of each other H, F, Cl or CN.

X' is preferably —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C— or a single bond, in particular —O—, —S—, —C≡C—, —CY$^1$=CY$^2$— or a single bond. In another preferred embodiment X' is a group that is able to form a conjugated system, such as —C≡C— or —CY$^1$=CY$^2$—, or a single bond.

Typical groups Sp' are, for example, —(CH$_2$)$_p$—, —(CH$_2$CH$_2$O)$_q$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, q being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethylene-oxyethylene, methyleneoxybutylene, ethylene-thioethylene, ethylene-N-methyl-iminoethylene, 1-methylalkylene, ethenylene, propenylene and butenylene for example.

The repeating units of formula I are preferably selected from the group consisting of the following subformulae:

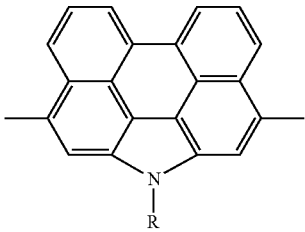

I1

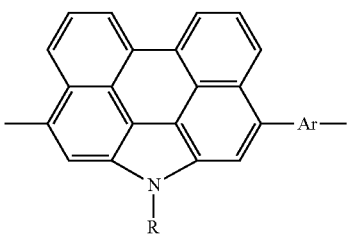

I2 wherein R and Ar are as defined in formula I, and the benzene rings are optionally substituted with one or more groups $R^1$ as defined in formula I.

The polymers of the present invention preferably comprise, very preferably consist of, one or more identical or different repeating units selected from the group consisting of formulae I, I1 and I2, and optionally one or more additional repeating units having the meaning of Ar as defined above and below.

The conjugated polymers are preferably selected of formula II

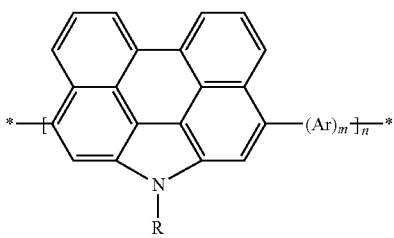

II wherein R, Ar and m on each occurrence identically or differently have the meanings of formula I, the benzene rings are optionally substituted with one or more groups $R^1$ as defined in formula I, and n is an integer >1.

The polymers of formula II are preferably selected from the group consisting of the following subformulae:

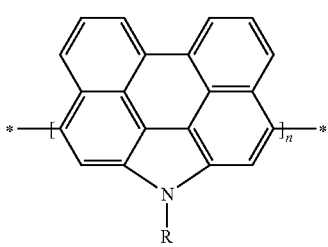

II1

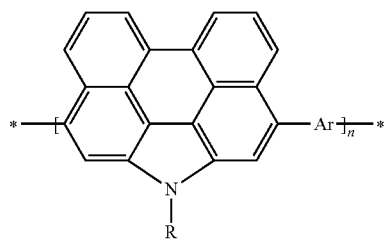

II2 wherein R, Ar and n have the meanings of formula II, and the benzene rings are optionally substituted with one or more groups $R^1$ as defined in formula I.

Especially preferred are polymers of formula IIa

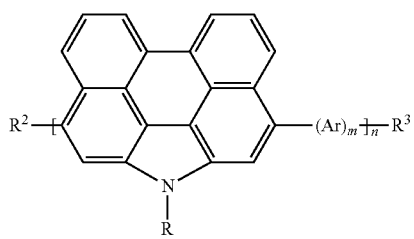

IIa wherein R, Ar, m and n on each occurrence identically or differently have the meanings of formula II, the benzene rings are optionally substituted with one or more groups $R^1$ as defined in formula I, and $R^2$ and $R^3$ have independently of each other one of the meanings of $R^1$, preferably H or halogen, or denote —CH$_2$Cl, —CHO, —CH=CH$_2$, —SiR'R"R''', —Sn-R'R"R''', —BR'R", —B(OR')(OR"), —B(OH)$_2$, or P-Sp, wherein P and Sp are as defined above, and R', R" and R''' have independently of each other one of the meanings of $R^0$ given above and R' and R" may also form a ring together with the hetero atom to which they are attached.

Further preferred are polymers of formula IIa-1:

$$R^2\text{-chain-}R^3 \qquad \text{IIa1}$$

wherein $R^2$ and $R^3$ are as defined in formula IIa, and "chain" is a polymer chain selected from the group consisting of formulae II1 and II2.

In the polymers according to the present invention, the total number of repeating units n is preferably ≥5, very preferably ≥10, most preferably ≥50, and preferably up to 500, very preferably up to 1,000, most preferably up to 2,000, including any combination of the aforementioned lower and upper limits of n.

The polymers of the present invention include homopolymers and copolymers, like statistical or random copolymers, alternating copolymers and block copolymers, as well as combinations thereof.

Block copolymers may for example comprise or consist of one or more blocks formed by units of formula I and one or more blocks formed by units Ar, wherein Ar has one of the meanings as described above and below.

Another aspect of the invention relates to monomers of formula III

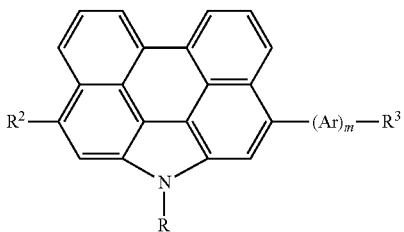

wherein R, $R^2$, $R^3$, Ar and m have the meanings of formula I or II or their subformulae, and the benzene rings are optionally substituted with one or more groups $R^1$ as defined in formula I.

Especially preferred are monomers of formula III selected from the following formulae:

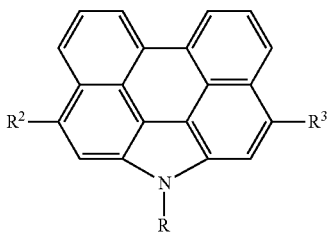

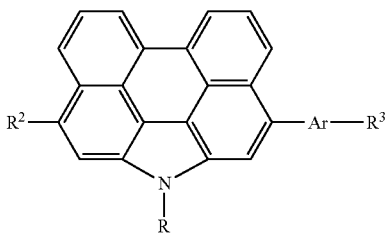

wherein R and Ar have one of the meanings of formula I, and the benzene rings are optionally substituted with one or more groups $R^1$ as defined in formula I.

Further preferred are monomers of formula III, III1 and III2 wherein $R^2$ and $R^3$ are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH and —Sn(Z$^4$)$_3$, wherein $Z^{1-4}$ are selected from the group consisting of alkyl and aryl, each being optionally substituted, and two groups $Z^2$ may also form a cyclic group.

Especially preferred are repeating units of formula I, polymers of formula II, and monomers of formula III, and their preferred subformulae as shown above and below, wherein m is 0, m is 1 or 2, Ar is selected from aryl or heteroaryl, preferably selected, on each occurrence identically or differently, from the group consisting of benzo[1,2,3]thiadiazole-4,7-diyl, benzo[1,2,3]selenadiazole-4,7-diyl, benzo[1,2,5]thiadiazole-4,7,diyl, benzo[1,2,5]selenadiazole-4,7,diyl, 4,7-di-thien-2-yl-benzo[1,2,3]thiadiazole, 4,7-di-thien-2-yl-benzo[1,2,5]thiadiazole, 2,3-dicyano-1,4-phenylene, 2,5-dicyano, 1,4-phenylene, 2,3-difluoro-1,4-phenylene, 2,5-difluoro, 1,4-phenylene, 2,3,5,6-tetrafluoro, 1,4-phenylene, 3,4-difluorothiophene-2,5-diyl, thieno[3,4-b]pyrazine-2,5-diyl, quinoxaline-5,8-diyl, selenophene-2,5-diyl, thiophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, 1,4-phenylene, pyridine-2,5-diyl, pyrimidine-2,5-diyl, p-p'-biphenyl, naphthalene-2,6-diyl, benzo[1,2-b:4,5-b]dithiophene-2,6-diyl, 2,2-dithiophene, 2,2-diselenophene, thiazole, oxazole, all of which are unsubstituted, mono- or polysubstituted, preferably with $R^1$ as defined above, especially preferably with m being 1, 2 or 3, n is at least 5, preferably at least 10, very preferably at least 50, and up to 2,000, preferably up to 500.

Mw is at least 5,000, preferably at least 8,000, very preferably at least 10,000, and preferably up to 300,000, very preferably up to 100,000, R is different from H, R is primary alkyl or alkoxy with 1 to 30 C atoms, secondary alkyl or alkoxy with 3 to 30 C atoms, or tertiary alkyl or alkoxy with 4 to 30 C atoms, wherein in all these groups one or more H atoms are optionally replaced by F, R is secondary alkyl with 3 to 29, preferably 3 to 21 C atoms, which is linked to the N-atom of the phenanthrocarbazole group via its central methylene unit, so that the two terminal alkyl chains have the same number of C atoms, and wherein one or more H atoms are optionally replaced by F, for example isopropyl, 3-pentyl, 4-heptyl, 5-nonyl, 6-undecyl, 7-tridecyl, 8-pentadecyl, 9-heptadecyl, 10-nonadecyl, R is aryl, alkylated aryl or alkoxy aryl with 4 to 40 C atoms, $R^2$ and $R^3$ are selected from H, halogen, —CH$_2$Cl, —CHO, —CH=CH$_2$—SiR'R"R''', —SnR'R"R''', —BR'R", —B(OR')(OR"), —B(OH)$_2$, P-Sp, C$_1$-C$_{20}$-alkyl, C$_1$-C$_{20}$-alkoxy, C$_2$-C$_{20}$-alkenyl, C$_1$-C$_{20}$-fluoroalkyl and optionally substituted aryl or heteroaryl, $R^2$ and $R^3$ are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^4$)$_2$, —C≡CH and —Sn(Z$^4$)$_3$, wherein Z" are selected from the group consisting of alkyl and aryl, each being optionally substituted, and two groups $Z^2$ may also form a cyclic group, $R^1$ is alkyl, alkoxy, alkylcarbonyl, alkylcarbonyloxy or alkoxycarbonyl with 1 to 30 C atoms, wherein one or more H atoms are optionally replaced by F, $R^1$ is H, R is P-Sp-, and/or the phenanthro[1,10,9,8-c,d,e,f,g]carbazole core is substituted by at least one group P-Sp-.

In a preferred embodiment Ar is a group comprising two or three aromatic or heteroaromatic rings that are fused or unfused, and are preferably selected form the rings disclosed above. Very preferably Ar according to this preferred embodiment is selected from the group consisting of the following subformulae, wherein $R^1$ is as defined above:

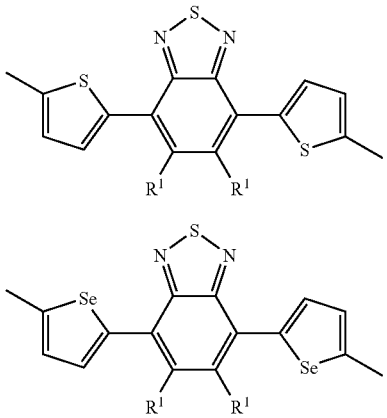

Accordingly, a preferred polymer of formula II2 wherein Ar is selected of formula IV1 has thus the following formula:

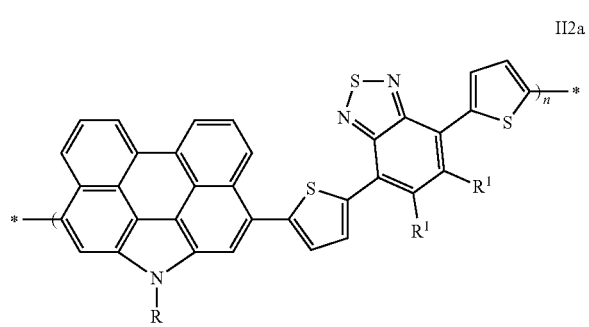

wherein R, R¹ and n have the meanings as described above and below.

The polymers of the present invention can be synthesized according to or in analogy to methods that are known to the skilled person and are described in the literature. Other methods of preparation can be taken from the examples. For example, they can be suitably prepared by aryl-aryl coupling reactions, such as Yamamoto coupling, Suzuki coupling, Stille coupling, Sonogashira coupling, Heck coupling or Buchwald coupling. Suzuki coupling and Yamamoto coupling are especially preferred.

The monomers which are polymerised to form the repeat units of the polymers can be prepared according to methods which are known to the person skilled in the art.

Preferably the polymers are prepared from monomers of formula III or its subformulae shown above.

Another aspect of the invention is a process for preparing a polymer by coupling one or more identical or different monomers based on a unit of formula I, preferably selected of formula III, IIIa or IIIa1, with each other and/or with one or more comonomers in a polymerisation reaction, preferably an aryl-aryl coupling reaction.

Suitable and preferred comonomers are those of the formula

R²—Ar—R³ wherein Ar, R² and R³ are as defined above.

Preferred methods for polymerisation are those leading to C—C-coupling or C—N-coupling, like Suzuki polymerisation, as described for example in WO 00/53656, Yamamoto polymerisation, as described in for example in T. Yamamoto et al., Progress in Polymer Science 1993, 17, 1153-1205 or in WO 2004/022626 A1, and Stille coupling. For example, when synthesizing a linear polymer by Yamamoto polymerisation, monomers as described above having two reactive halide groups $R^{7,8}$ is preferably used. When synthesizing a linear polymer by Suzuki polymerisation, preferably a monomer as described above is used wherein at least one reactive group $R^{7,8}$ is a boronic acid or boronic acid derivative group.

Suzuki polymerisation may be used to prepare homopolymers as well as statistical, alternating and block random copolymers. Statistical or block copolymers can be prepared for example from the above monomers of formula II wherein one of the reactive groups $R^2$ and $R^3$ is halogen and the other reactive group is a boronic acid or boronic acid derivative group. The synthesis of statistical, alternating and block copolymers is described in detail for example in WO 03/048225 A2 or WO 2005/014688 A2.

Suzuki polymerisation employs a Pd(0) complex or a Pd(II) salt. Preferred Pd(0) complexes are those bearing at least one phosphine ligand such as $Pd(Ph_3P)_4$. Another preferred phosphine ligand is tris(ortho-tolyl)phosphine, i.e. $Pd(o-Tol)_4$. Preferred Pd(II) salts include palladium acetate, i.e. $Pd(OAc)_2$. Suzuki polymerisation is performed in the presence of a base, for example sodium carbonate, potassium phosphate or an organic base such as tetraethylammonium carbonate. Yamamoto polymerisation employs a Ni(0) complex, for example bis(1,5-cyclooctadienyl) nickel(0).

As alternatives to halogens as described above, leaving groups of formula —O—SO₂Z¹ can be used wherein Z¹ is as described above. Particular examples of such leaving groups are tosylate, mesylate and triflate.

Especially suitable and preferred synthesis methods of the repeating units and monomers of formula I and III, and their homo- and co-polymers of formula II are illustrated in the synthesis schemes shown hereinafter. Therein R has one of the meanings of R¹ given in formula I.

The generic synthesis of the poly-2,7-(phenanthro[1,10,9,8-c,d,e,f,g]carbazole) units with solubilizing groups and subsequent polymers is exemplarily shown in Scheme 1 and 2 below.

Preferably the synthesis of the phenanthro[1,10,9,8-c,d,e,f,g]carbazole units is carried out according to previously described procedures in the literature,[11,12] followed by either an alkylation or arylation reaction to incorporate the solubilizing group, as illustrated in Scheme 1. The double halogenation reaction is followed by either a double lithium halogen exchange reaction or palladium catalyst reaction in presence of a boron source to obtain the double boronic acid or ester functionalized product.

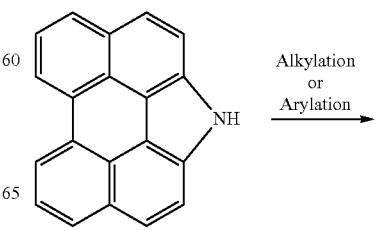

17
-continued

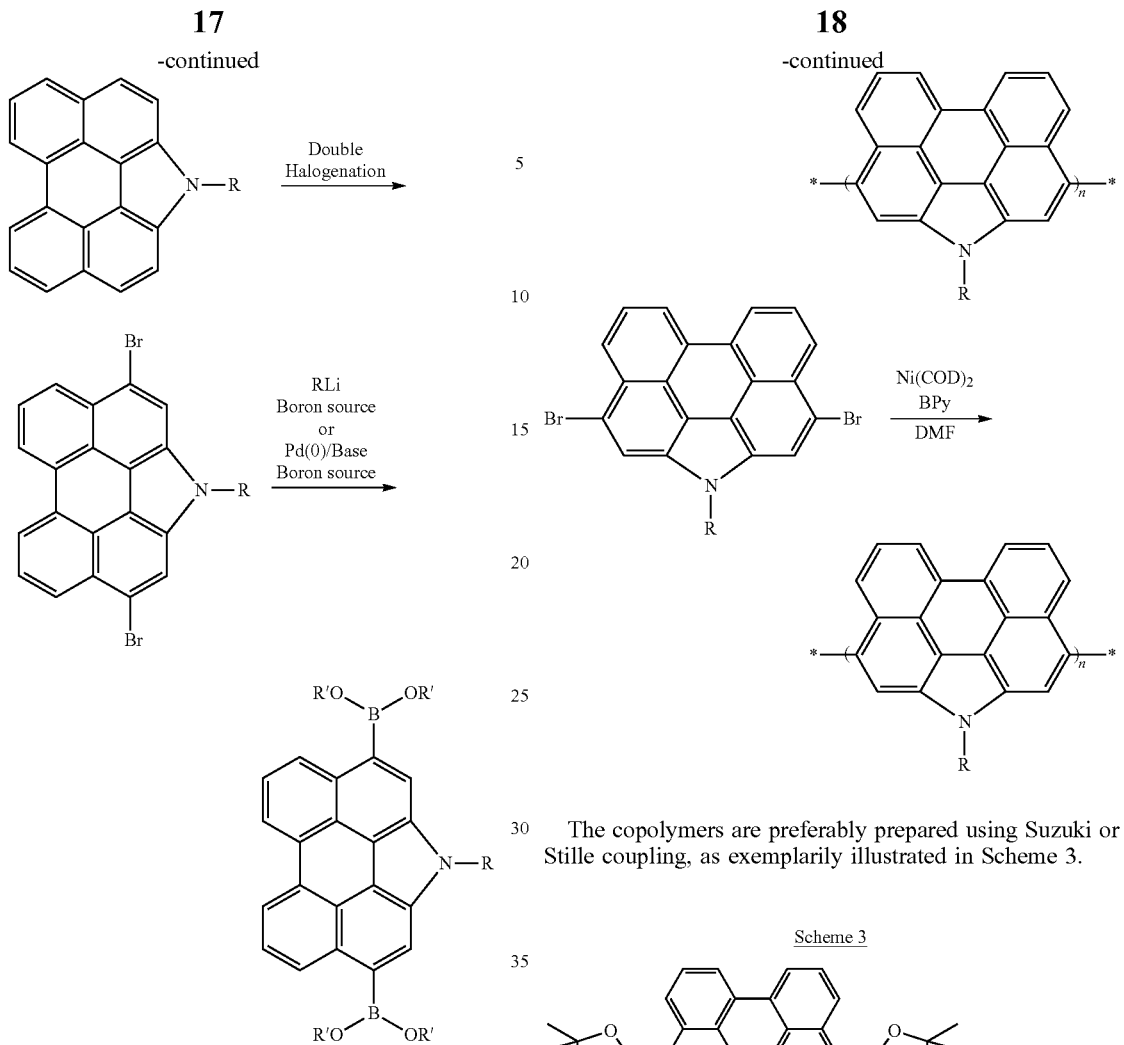

The polymers can be synthesized by various organometallic catalyzed reaction such as Yamamoto,[16,17] Suzuki[18] or Stille[19] coupling. The homopolymers are preferably synthesized using Yamamoto or Suzuki coupling, as illustrated in Scheme 2.

18
-continued

The copolymers are preferably prepared using Suzuki or Stille coupling, as exemplarily illustrated in Scheme 3.

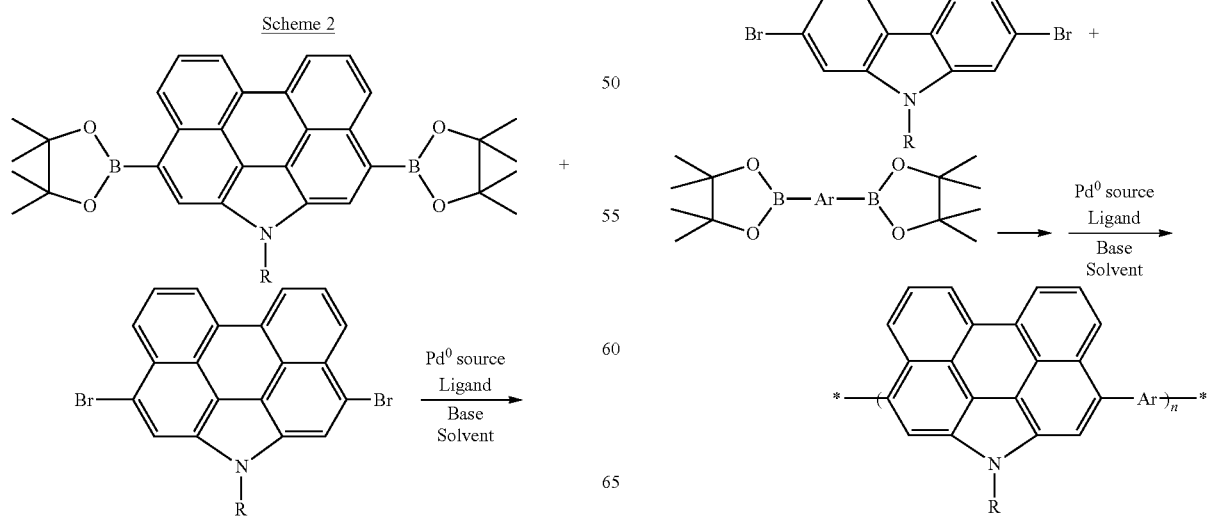

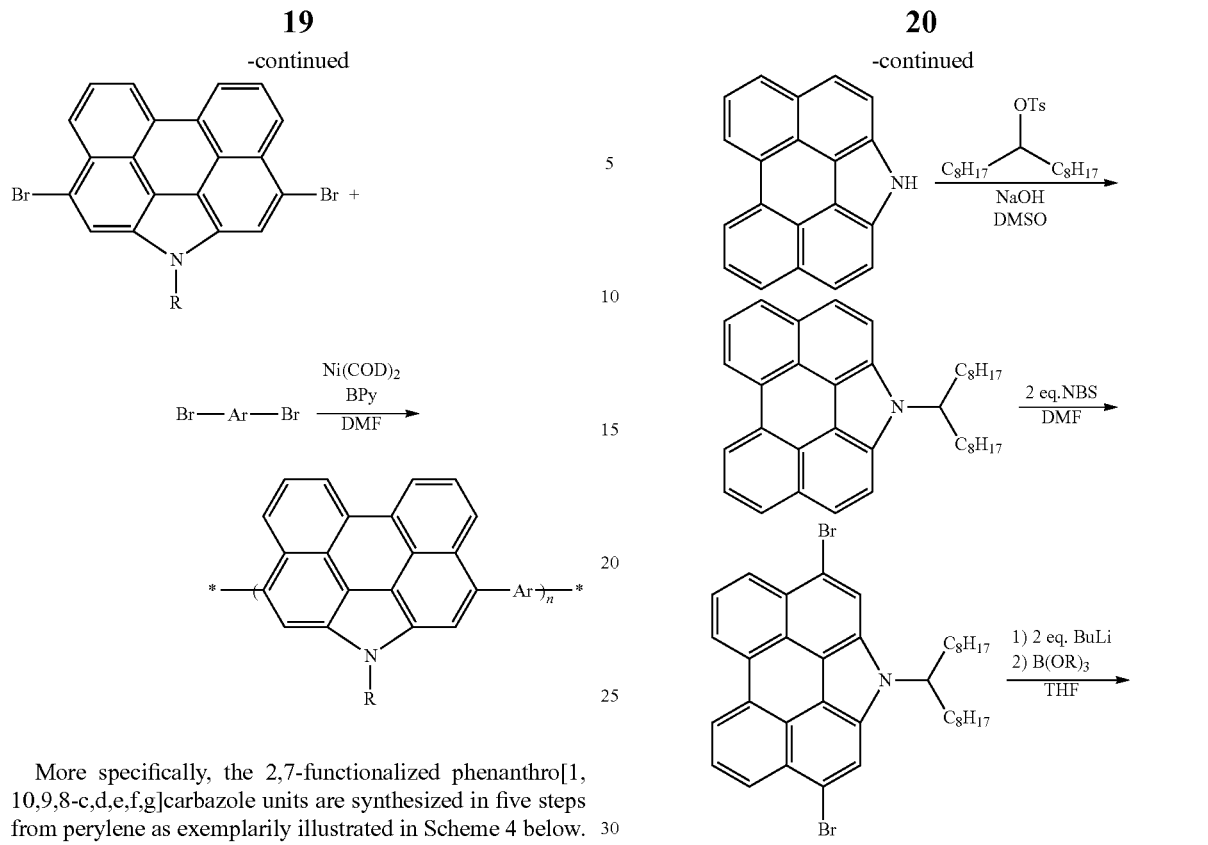

More specifically, the 2,7-functionalized phenanthro[1,10,9,8-c,d,e,f,g]carbazole units are synthesized in five steps from perylene as exemplarily illustrated in Scheme 4 below. Perylene is first nitrated, resulting in a mixture of both the 1-nitro and 3-nitroperylene following literature procedures.[11,12] The crude product is reacted with the triethylphosphite in presence of methanesulfonic acid to obtain the phenanthro[1,10,9,8-c,d,e,f,g]carbazole. This product is alkylated using 9-heptadecane p-toluenesulfonate,[8,22] then brominated using N-bromosuccimide as a halogen source in dimethylformamide. The final product is synthesized via a double lithium halogen exchange following by the addition of the 2-isopropoxy-4,4,5,5-tetramethyl-1,3,2-dioxaborolane. The polymer is prepared using a Suzuki coupling polymerization.[23]

Scheme 4

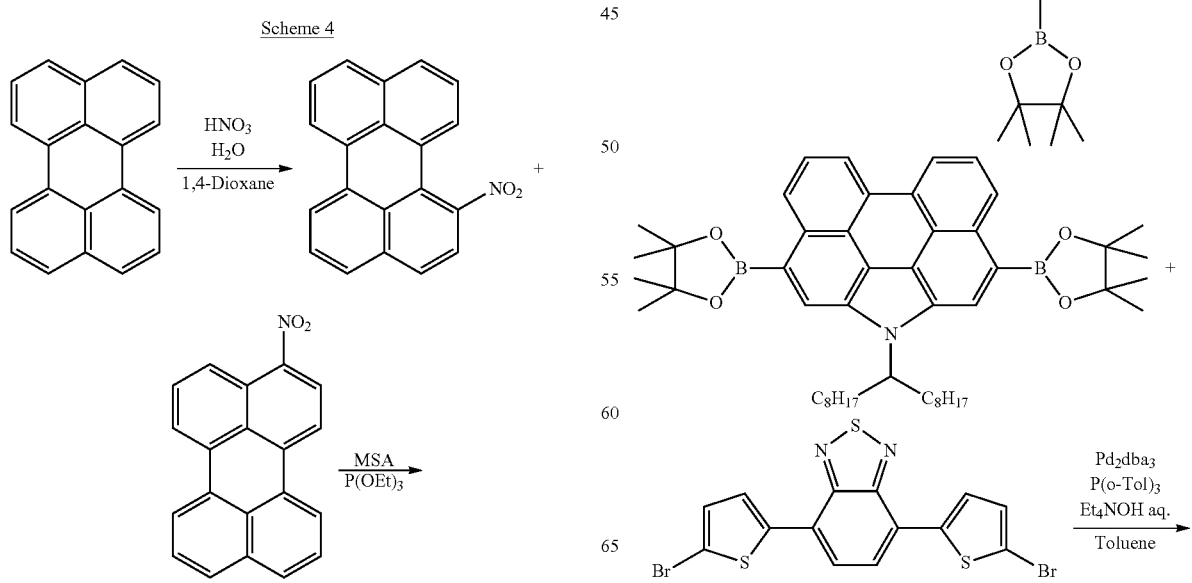

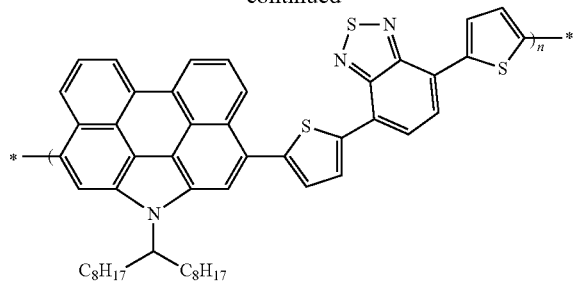

The novel methods of preparing monomers and polymers as described above and below are another aspect of the invention.

The polymers according to the present invention can also be used in polymer blends, for example together with other polymers having charge-transport, semiconducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising one or more polymers or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylansiole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxybenzene, 1-methylnaphthalene, N-methylpyrrolidinone, 3-fluorobenzotrifluoride, benzotrifluoride, benzotrifluoride, diosane, trifluoromethoxybenzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents with high boiling temperatures and solvent mixtures are preferred. For spin coating alkylated benzenes like xylene and toluene are preferred.

Examples of especially preferred solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and/or mixtures thereof.

The concentration of the polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 38, No 496, 296 (1966)". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, letter-press printing, screen printing, doctor blade coating, roller printing, reverse-roller printing, offset lithography printing, flexographic printing, web printing, spray coating, brush coating or pad printing. Ink-jet printing is particularly preferred as it allows high resolution layers and devices to be prepared.

Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents methoned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the polymer, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymers or formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The polymers according to the present invention are useful as charge transport, semiconducting, electrically conducting, photoconducting or light mitting materials in optical, electrooptical, electronic, electroluminescent or photoluminescent components or devices. In these devices, the polymers of the present invention are typically applied as thin layers or films.

Thus, the present invention also provides the use of the semiconducting polymer, polymer blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a polymer, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a polymer, polymer blend, formulation or organic semiconducting layer according to the present invention. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs and OPV devices. For example, the active semiconductor channel between the drain and source in an OFET may comprise the layer of the invention. As another example, a charge (hole or electron) injection or transport layer in an OLED device may comprise the layer of the invention. The formulations according to the present invention and layers formed therefrom have particular utility in OFETs especially in relation to the preferred embodiments described herein.

The compound, formulation and layer of the present invention are especially suitable for use in an organic field effect transistor OFET as the semiconducting channel. Accordingly, the invention also provides an organic field effect transistor (OFET) comprising a gate electrode, an insulating (or gate insulator) layer, a source electrode, a drain electrode and an organic semiconducting channel connecting the source and drain electrodes, wherein the organic semiconducting channel comprises a polymer, polymer blend, formulation or organic semiconducting layer according to the present invention. Other features of the OFET are well known to those skilled in the art.

OFETs where an organic semiconducting (OSC) material is arranged as a thin film between a gate dielectric and a drain and a source electrode, are generally known, and are described for example in U.S. Pat. No. 5,892,244, U.S. Pat. No. 5,998,804, U.S. Pat. No. 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
 a source electrode,
 a drain electrode,
 a gate electrode,
 a semiconducting layer,
 one or more gate insulator layers,
 optionally a substrate.
wherein the semiconductor layer preferably comprises a polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF®, 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

An OPV device according to the present invention preferably comprises:
- a low work function electrode (for example Aluminum),
- a high work function electrode (for example ITO), one of which is transparent,
- a bilayer of consisting of a hole transporting and an electron transporting material; the bilayer can exist as two distinct layers or as a blended mixture, a so-called bulk heterjunction (BHJ) (see for example Coakley, K. M. and McGehee, M. D. Chem. Mater. 2004, 16, 4533),
- an optional conducting polymer layer (such as for example PEDOT:PSS) to modify the work function of the high work function electrode to provide an ohmic contact for the hole,
- an optional coating on the high workfunction electrode (such as LiF) to provide an ohmic contact for electrons.

The hole transporting material is constituted by a compound of the present invention. The electron transporting material can be an inorganic material such as zinc oxide or cadmium selenide, or an organic material such as a fullerene derivate (for example PCBM, [(6,6)-phenyl C61-butyric acid methyl ester] or a polymer see for example Coakley, K. M. and McGehee, M. D. Chem. Mater. 2004, 16, 4533). For the blended mixture, an optional annealing step may be necessary to optimize blend morpohology and consequently OPV device performance.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the materials according to the invention can be used in organic light emitting devices or diodes (OLEDs), e.g., in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111-112, 2000, 31-34, Alcala, J. Appl. Phys., 88, 2000, 7124-7128 and the literature cited therein.

According to another use, the materials according to the present invention, especially those which show photoluminescent properties, may be employed as materials of light sources, e.g., of display devices such as described in EP 0 889 350 A1 or by C. Weder et al., Science, 279, 1998, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^{-1}$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention may also be suitable for use in organic plasmon-emitting diodes (OPEDs), as described for example in Koller et al., Nature Photonics 2008 (published online Sep. 28, 2008).

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, Proc. Natl. Acad. Sci. U.S.A. 1999, 96, 12287; D. Wang, X. Gong, P. S. Heeger, F. Rininsland, G. C. Bazan and A. J. Heeger, Proc. Natl. Acad. Sci. U.S.A. 2002, 99, 49; N. DiCesare, M. R. Pinot, K. S. Schanze and J. R. Lakowicz, Langmuir 2002, 18, 7785; D. T. McQuade, A. E. Pullen, T. M. Swager, Chem. Rev. 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

REFERENCES (1) Blouin, N.; Leclerc, M. *Acc. Chem. Res.* 2008, 41, 1110-1119.

(2) Morin, J.-F.; Leclerc, M.; Adès, D.; Siove, A. *Macromol. Rapid Commun.* 2005, 26, 761-778.

(3) Cho, S. H.; Song, K. T.; Lee, J. Y. In *Handbook of Conducting Polymers*; Skotheim, T. A., Reynolds, J. R., Eds.; CRC Press LLC: Boca Raton, Fla., 2007; Vol. 1, p 8/1-8/87.

(4) Boudreault, P.-L.; Blouin, N.; Leclerc, M. *Adv. Polym. Sci.* 2008, 212, 99-124.

(5) Grazulevicius, J. V.; Strohriegl, P.; Pielichowski, J.; Pielichowski, K. *Prog. Polym. Sci.* 2003, 28, 1297-1353.

(6) Morin, J. F.; Leclerc, M. *Macromolecules* 2001, 34, 4680-4682.

(7) Blouin, N.; Michaud, A.; Gendron, D.; Wakim, S.; Blair, E.; Neagu-Plesu, R.; Belletête, M.; Durocher, G.; Tao, Y.; Leclerc, M. *J. Am. Chem. Soc.* 2008, 130, 732-742.

(8) Blouin, N.; Michaud, A.; Leclerc, M. *Adv. Mater.* 2007, 19, 2295-2300.

(9) Park, S. H.; Roy, A.; Beaupre, S.; Cho, S.; Coates, N.; Moon, J. S.; Moses, D.; Leclerc, M.; Lee, K.; Heeger, A. J. *Nat. Photon.* 2009, 3, 297-302.

(10) Li, Y.; Wang, Z. *Org. Lett.* 2009, 11, 1385-1387.

(11) Jiang, W.; Qian, H.; Li, Y.; Wang, Z. *J. Org. Chem.* 2008, 73, 7369-7372.

(12) Looker, J. J. *J. Org. Chem.* 1972, 37, 3379-3381.

(13) Sun, Y.; Tan, L.; Jiang, S.; Qian, H.; Wang, Z.; Yan, D.; Di, C.; Wang, Y.; Wu, W.; Yu, G.; Yan, S.; Wang, C.; Hu, W.; Liu, Y.; Zhu, D. *J. Am. Chem. Soc.* 2007, 129, 1882-1883.

(14) Sirringhaus, H.; Brown, P. J.; Friend, R. H.; Nielsen, M. M.; Bechgaard, K.; Langeveld-Voss, B. M. W.; Spiering, A. J. H.; Janssen, R. A. J.; Meijer, E. W.; Herwig, P.; de Leeuw, D. M. *Nature* 1999, 401, 685-688.

(15) Scherf, U.; List, E. J. W. *Adv. Mater.* 2002, 14, 477-487.

(16) Yamamoto, T.; Morita, A.; Miyazaki, Y.; Maruyama, T.; Wakayama, H.; Zhou, Z. H.; Nakamura, Y.; Kanbara, T.; Sasaki, S.; Kubota, K. *Macromolecules* 1992, 25, 1214-1223.

(17) Yamamoto, T.; Takimiya, K. *J. Am. Chem. Soc.* 2007, 129, 2224-2225.

(18) Schlüter, A. D. *J. Polym. Sci., Part A: Polym. Chem.* 2001, 39, 1533-1556.

(19) Bao, Z.; Chan, W. K.; Yu, L. *J. Am. Chem. Soc.* 1995, 117, 12426-12435.

(20) Mullekom, H. A. M. v.; Vekemans, J. A. J. M.; Having a, E. E.; Meijer, E. W. *Mater. Sci. Eng., R.* 2001, 32, 1-40.

(21) Dennler, G.; Scharber, M. C.; Brabec, C. J. *Adv. Mater.* 2009, 21, 1323-1338.

(22) Marzoni, G.; Garbrecht, W. L. *Synthesis* 1987, 651-653.

(23) Towns, C.; Wallace, P.; Allen, I.; Pounds, T.; Murtagh, L., Modified Suzuki-method for polymerization of aromatic monomers, U.S. Pat. No. 7,173,103

The invention will now be described in more detail by reference to the following examples, which are illustrative only and do not limit the scope of the invention.

Example 1

Poly[N-9'-heptadecylphenanthro[1,10,9,8-c,d,e,f,g]carbazole-alt-5,5-(4',7'-di-2-thienyl-2',1',3'-benzothiadiazole)] 1 was prepared as described below

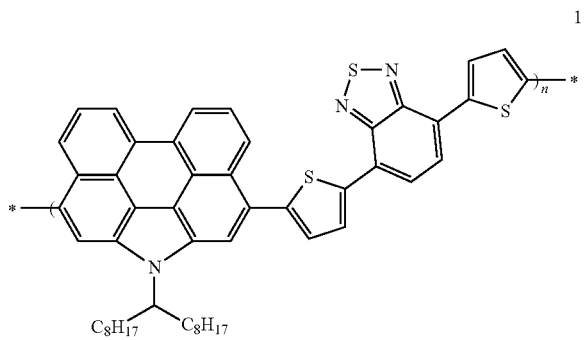

1

N-Hydro-phenanthro[1,10,9,8-c,d,e,f,g]carbazole

To a hot solution of perylene (25.0 g, 99.1 mmol) in 1,4-dioxane (1000 cm$^3$) was added a mixture of water (20.0 cm$^3$) and nitric acid (12.5 cm$^3$, d=1.5) dropwise. The resulting solution was heated to 60° C. with vigorous stirring for 25-30 mins, and then cooled and poured into water (4000 cm$^3$). The solid was collected, washed and dried to afford a mixture of 1-nitroperylene (26%, GC-MS) and 3-nitroperylene (74% GC-MS) as a brick-red powder (29.1 g). The powder is suspended in triethylphosphite (130 cm$^3$) and methanesulfonic acid (6.1 cm$^3$). The mixture is heated to 200° C. overnight and then the solution is cooled down. The excess of triethylphosphite is removed under vacuum and the product is recovered after column chromatography (silica gel, toluene as eluent). The product is further purified by trituration in hot toluene (125 cm$^3$) to afford the title product (5.12 g, yield 22% over two steps). NMR ($^1$H, 300 MHz, Acetone-d$_6$): δ 12.20 (s, 1H); 8.76 (d, J=7.4 Hz, 2H); 8.18 (d, J=8.1 Hz, 2H); 7.98 (d, J=8.7 Hz, 2H); 7.95 (d, J=8.7 Hz, 2H); 7.83 (t, J=7.8 Hz, 2H).

N-9'-Heptadecylphenanthro[1,10,9,8-c,d,e,f,g]carbazole

A dried three neck flask fitted with an addition funnel was charged with N-hydro-phenanthro[1,10,9,8-c,d,e,f,g]carbazole (2.50 g, 9.42 mmol), dimethyl sulfoxide (23 cm$^3$) and freshly powdered potassium hydroxide (2.64 g, 47.1 mmol). When the phenanthro[1,10,9,8-c,d,e,f,g]carbazole was completely dissolved, a solution of 9-heptadecane p-toluenesulfonate (5.80 g, 14.1 mmol) in DMSO (15 cm$^3$) was added dropwise through the addition funnel over 1-1.5 hours at 25° C. After 18 hours, the reaction was poured into distilled water (200 cm$^3$) and the aqueous layer was extracted three times with petroleum ether (3×250 mL). The combined organic fractions were dried over magnesium sulfate and the solvent was removed under reduced pressure. The crude product was dissolved in dichloromethane, pre-adsorbed on silica gel, and purified by column chromatography (silica gel, petroleum ether as eluant) resulting in a yellow solid. (3.75 g, yield 79%). NMR ($^1$H, 300 MHz, o-DCB-d$_4$): δ 8.66 (d, J=7.5 Hz, 2H); 8.17 (d, J=7.9 Hz, 2H); 7.98 (s, 2H); 7.97 (s, 2H); 7.87 (t, J=7.7 Hz, 2H); 4.88 (m, 1H); 2.48 (m, 2H); 2.15 (m, 2H); 1.24 (br, 24H); 0.89 (t, J=6.9 Hz, 6H).

2,7-Dibromo-N-9'-heptadecylphenanthro[1,10,9,8-c,d,e,f,g]carbazole

A dried round bottom flask was charged with N-9'-heptadecylphenanthro[1,10,9,8-c,d,e,f,g]carbazole (3.00 g, 5.96 mmol) and dichloromethane (300 cm$^3$). To this solution, N-bromosuccimide (2.12 g, 11.9 mmol) is added slowly in three portions. The solution was stirred for 25 mins at 25° C. and then the solvent removed under vacuum. The crude product is pre-absorbed on silica gel and purified by column chromato-graphy (silica gel, petroleum ether as eluent) to afford the title product as a yellow solid (2.71 g, yield 69%). NMR ($^1$H, 300 MHz, o-DCB-d$_4$): δ 8.66 (d, J=7.5 Hz, 2H); 8.42 (d, J=8.2 Hz, 2H); 8.39 (s, 2H); 7.92 (t, J=7.9 Hz, 2H), 4.73 (m, 1H); 2.37 (m, 2H); 2.11 (m, 2H); 1.14 (br, 24H); 0.89 (t, J=6.9 Hz, 6H).

2,7-Bis(4,4,5,5-tetramethyl-1,3,2-dioxaborolan-2-yl)-N-9'-heptadecylphenanthro[1,10,9,8-c,d,e,f,g]carbazole A dried round bottom flaks was charged with 2,7-dibromo-N-9'-heptadecylphenanthro[1,10,9,8-c,d,e,f,g]carbazole (1.00 g, 1.51 mmol) and tetrahydrofuran (15 cm$^3$). The resulting solution was cooled down to −78° C., then n-butyllithium (2.5M in hexanes, 1.24 cm$^3$, 3.10 mmol) was added dropwise over 10 mins. The mixture was stirred at −78° C. for 1 hour, then 2-isopropoxy-4,4,5,5-tetramethyl-1,3,2-dioxaborolane (0.68 cm$^3$ 3.32 mmol) was added rapidly to the solution. After an additional 1 hour at −78° C., the resulting mixture was warmed to room temperature and stirred overnight. The mixture was poured into water, extracted with diethyl ether four times and dried over magnesium sulfate. The solvent was removed under reduced pressure, and the residue was purified by recrystallisation from isopropyl alcohol:acetone (ca. 3:1) to obtain the title product as a yellow crystalline solid (0.423 g, yield 37%). NMR ($^1$H, 300 MHz, CDCl$_3$): δ 8.98 (d, J=8.2 Hz, 2H); 8.68 (d, J=7.5 Hz, 2H); 8.46 (s, 2H); 7.86 (t, J=7.9 Hz, 2H), 4.90 (m, 1H); 2.42 (m, 2H); 2.12 (m, 2H); 1.49 (s, 24H); 1.10 (br, 24H); 0.77 (t, J=6.7 Hz, 6H).

Poly[N-9'-heptadecylphenanthro[1,10,9,8-c,d,e,f,g]carbazole-alt-5,5-(4',7'-di-2-thienyl-2',1',3'-benzothiadiazole)] 1

In a dried flask, 2,7-bis(4,4,5,5-tetramethyl-1,3,2-dioxaborolan-2-yl)-N-9'-heptadecylphenanthro[1,10,9,8-c,d,e,f,g]carbazole (300.0 mg, 0.3970 mmol), 4,7-di(2'-bromothien-5'-yl)-2,1,3-benzothiadiazole (181.9 mg, 0.3970 mmol), tris(dibenzylideneacetone)dipalladium(0) (1.8 mg, 0.0020 mmol) and tri(o-tolyl)phosphine (2.4 mg, 0.0079 mmol) were dissolved in degassed toluene (4.0 cm$^3$) and degassed 20% aqueous tetraethylammonium hydroxide (1.25 cm$^3$). The reaction mixture was vigorously stirred at 100-105° C. for 24 hours. The polymer was purified by precipitation into methanol:water (10:1), filtered and washed sequentially via Soxhlet extraction with acetone, petroleum ether, cyclohexane and chloroform. The chloroform fraction was reduced to a smaller volume under reduced pressure and precipitated into methanol (500 cm$^3$). The precipitated polymer was filtered and dried under vacuum at 25° C. over night to afford the title product 1 (192 mg, yield 60%). M$_n$=6,100 g/mol, M$_w$=12,300 g/mol. λ$_{max}$=582 nm (solid state), 550 nm (chlorobenzene).

Example 2

Poly[2,7-N-1'-dodecyl-tridecylphenanthro[1,10,9,8-c,d,e,f,g]carbazole-alt-5,5-(4',7'-di-2-thienyl-2',1',3'-benzothiadiazole)] 2 was prepared as described below

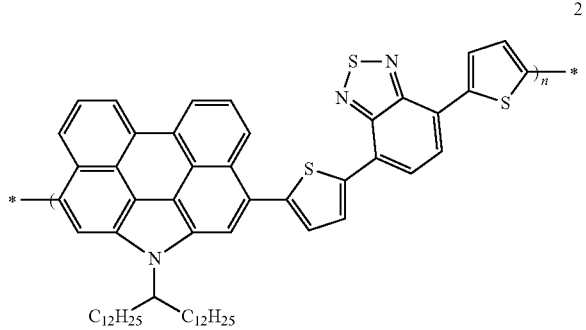

2

N-1'-Dodecyl-tridecylphenanthro[1,10,9,8-c,d,e,f,g]carbazole

A dried three neck flask fitted with an addition funnel was charged with N-hydro-phenanthro[1,10,9,8-c,d,e,f,g]carbazole (4.00 g, 15.1 mmol), dimethyl sulfoxide (36 cm$^3$) and freshly powdered potassium hydroxide (2.64 g, 47.1 mmol). When the phenanthro[1,10,9,8-c,d,e,f,g]carbazole was completely dissolved, a solution of 9-heptadecane p-toluenesulfonate (11.8 g, 22.6 mmol) in DMSO (24 cm$^3$) was added dropwise through the addition funnel over 2.5 hours at 45° C. After 18 hours, the reaction was poured into distilled water (200 cm$^3$) and the aqueous layer was extracted three times with dichloromethane (3×250 cm$^3$). The combined organic fractions were dried over magnesium sulfate and the solvent was removed under reduced pressure. The crude product was dissolved in dichloromethane, pre-adsorbed on silica gel, and purified by column chromatography (silica gel, 100:0 to 80:20, petroleum ether:ethyl acetate as eluent) resulting the title product as a yellow solid (3.01 g, yield 32%). NMR ($^1$H, 300 MHz, CDCl$_3$): δ 8.63 (d, J=7.5 Hz, 2H); 8.09 (d, J=8.0 Hz, 2H); 7.86 (d, J=8.9 Hz, 2H); 7.79 (m, 4H); 4.70 (m, 1H); 2.32 (m, 2H); 2.00 (m, 2H); 1.17 (br, 40H); 0.84 (t, J=6.8 Hz, 6H).

2,7-Dibromo-N-1'-dodecyl-tridecylphenanthro[1,10,9,8-c,d,e,f,g]carbazole

A dried round bottom flask was charged with N-1'-dodecyl-tridecylphenanthro[1,10,9,8-c,d,e,f,g]carbazole (2.60 g, 4.22 mmol) and dichloromethane (210 cm$^3$). To this solution, N-bromosuccinimide (1.50 g, 8.44 mmol) was added slowly. The solution was stirred for 35 minutes at 25° C. and then the solvent was removed under vacuum. The crude product was pre-absorbed on silica gel and purified by column chromatography (silica gel, petroleum ether as eluent) to afford the title product as a yellow solid (2.95 g, yield 90%). NMR ($^1$H, 300 MHz, CDCl$_3$): δ 8.63 (d, J=7.5 Hz, 2H); 8.34 (d, J=8.2 Hz, 2H); 8.15 (s, 2H); 7.86 (t, J=7.9 Hz, 2H), 4.63 (m, 1H); 2.28 (m, 2H); 2.02 (m, 2H); 1.14 (br, 40H); 0.84 (t, J=6.9 Hz, 6H).

2,7-Bis(4,4,5,5-tetramethyl-1,3,2-dioxaborolan-2-yl)-N-1'-dodecyl-tridecylphenanthro[1,10,9,8-c,d,e,f,g]carbazole A dried round bottom flaks was charged with 2,7-dibromo-N-1'-dodecyl-tridecylphenanthro[1,10,9,8-c,d,e,f,g]carbazole (2.00 g, 2.59 mmol) and tetrahydrofuran (26 cm$^3$). The resulting solution was cooled down to −78° C., then n-butyllithium (2.5M in hexanes, 2.12 cm$^3$, 5.30 mmol) was added dropwise over 10 mins. The mixture was stirred at −78° C. for 1 hour, then 2-isopropoxy-4,4,5,5-tetramethyl-1,3,2-dioxaborolane (1.16 cm$^3$ 5.69 mmol) was added rapidly to the solution. After an additional 1 hour at −78° C., the resulting mixture was warmed to room temperature and stirred overnight. The mixture was poured into water, extracted with diethyl ether four times and dried over magnesium sulfate. The solvent was removed under reduced pressure, and the residue was purified by column chromatography (silica gel, 95:5 to 75:25, petroleum ether:dichloromethane with 1% triethylamine as eluent) to obtain the title product as a yellow crystalline solid (1.125 g, yield 50%). NMR ($^1$H, 300 MHz, CDCl$_3$): δ 8.98 (d, J=8.2 Hz, 2H); 8.68 (d, J=7.5 Hz, 2H); 8.46 (s, 2H); 7.86 (t, J=7.9 Hz, 2H), 4.90 (m, 1H); 2.42 (m, 2H); 2.12 (m, 2H); 1.49 (s, 24H), 1.10 (br, 24H); 0.77 (t, J=6.7 Hz, 6H).

Poly[2,7-N-1'-dodecyl-tridecylphenanthro[1,10,9,8-c,d,e,f,g]carbazole-alt-5,5-(4',7'-di-2-thienyl-2',1',3'-benzothiadiazole)] 2

In a dried flask, 2,7-bis(4,4,5,5-tetramethyl-1,3,2-dioxaborolan-2-yl)-N-1'-dodecyl-tridecylphenanthro[1,10,9,8-c,d,e,f,g]carbazole (607.5 mg, 0.7000 mmol), 4,7-di(2'-bromothien-5'-yl)-2,1,3-benzothiadiazole (320.8 mg, 0.7000 mmol), tris(dibenzylideneacetone)dipalladium(0) (3.2 mg, 0.0035 mmol) and tri(o-tolyl)phosphine (4.3 mg, 0.0140 mmol) were dissolved in degassed toluene (7.0 cm$^3$) and degassed 20% aqueous tetraethylammonium hydroxide (2.2 cm$^3$). The reaction mixture was vigorously stirred at 100-105° C. for 24 hours. The polymer was purified by precipitation into methanol:water (10:1), filtered and washed sequentially via Soxhlet extraction with acetone, petroleum ether, cyclohexane and chloroform. The chloroform fraction was reduced to a smaller volume under reduced pressure and precipitated into methanol (500 cm$^3$). The precipitated polymer was filtered and dried under vacuum at 25° C. overnight to afford the title product 2 (365 mg, yield 57%). $M_n$=5,800 g/mol, $M_w$=12,000 g/mol. $\lambda_{max}$=588 nm (solid state), 557 nm (chlorobenzene).

Example 3

Poly[2,7-N-octylphenanthro[1,10,9,8-c,d,e,f,g]carbazole-alt-5,5-(4',7'-di-2-thienyl-2',1',3'-benzothiadiazole)] 3 was prepared as described below

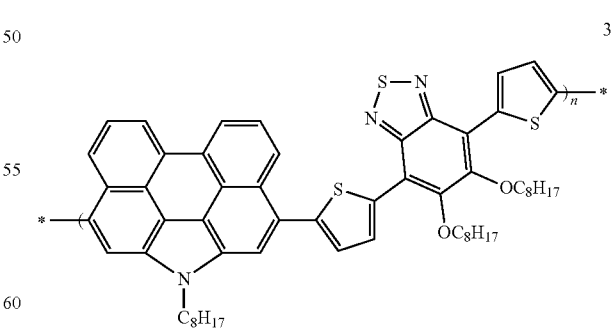

3

N-Octylphenanthro[1,10,9,8-c,d,e,f,g]carbazole

A dried flask fitted with a condenser was charged with N-hydro-phenanthro[1,10,9,8-c,d,e,f,g]carbazole (3.50 g, 13.2 mmol), bromooctane (2.51 cm³, 14.5 mmol), tetrabutylammonium bromide (0.213 g, 0.660 mmol), freshly powdered sodium hydroxide (1.055 g, 26.4 mmol) and acetone (130 cm³). The resulting solution was reflux for 4 hours and then poured into distilled water (100 cm³). The resulting solution was extracted with dichloromethane (3×200 cm³). The combined organic fractions were dried over magnesium sulfate and the solvent was removed under reduced pressure. The crude product was dissolved in dichloromethane, pre-adsorbed on silica gel, purified by column chromatography (silica gel, 95:5 to 90:10, petroleum ether:ethyl acetate as eluent) and recrystallized into methanol and toluene resulting in the title product as a yellow solid. (2.37 g, yield 48%). NMR (¹H, 300 MHz, CDCl₃): δ 8.65 (d, J=7.5 Hz, 2H); 8.12 (d, J=8.0 Hz, 2H); 7.92 (d, J=8.8 Hz, 2H); 7.81 (d, J=8.9 Hz, 2H); 7.79 (d, J=7.8 Hz, 2H); 4.72 (t, J=8.8 Hz, 2H); 2.10 (m, 2H); 1.36 (br, 4H); 1.22 (br, 6H); 0.83 (t, J=6.8 Hz, 3H).

2,7-Dibromo-N-octylphenanthro[1,10,9,8-c,d,e,f,g]carbazole

A dried round bottom flask was charged with N-octylphenanthro[1,10,9,8-c,d,e,f,g]carbazole (2.40 g, 6.36 mmol) and dichloromethane (320 cm³). To this solution, N-bromosuccimide (2.26 g, 12.7 mmol) was added slowly. The solution was stirred for 60 minutes at 25° C. and then poured into distilled water (200 cm³). The resulting solution was extracted with dichloromethane (2×100 cm³). The combined organic fractions were dried over magnesium sulfate and the solvent was removed under reduced pressure. The resulting oil was dissolved into a minimal dichloromethane volume and precipitate into methanol (300 cm³) to afford the title product as a yellow solid after filtration (2.83 g, yield 83%). NMR (¹H, 300 MHz, CDCl₃): δ 8.56 (d, J=7.5 Hz, 2H); 8.27 (d, J=8.3 Hz, 2H); 7.96 (s, 2H); 7.84 (t, J=7.9 Hz, 2H), 4.45 (t, J=7.0 Hz, 2H); 1.98 (m, 2H); 1.31 (br, 4H); 1.22 (br, 6H); 0.83 (t, J=6.8 Hz, 3H).

2,7-Bis(4,4,5,5-tetramethyl-1,3,2-dioxaborolan-2-yl)-N-octylphenanthro[1,10,9,8-c,d,e,f,g]carbazole A dried round bottom flaks was charged with 2,7-dibromo-N-octylphenanthro[1,10,9,8-c,d,e,f,g]carbazole (2.00 g, 3.74 mmol) and tetrahydrofuran (37 cm³). The resulting solution was cooled down to −78° C., then n-butyllithium (2.5M in hexanes, 3.06 cm³, 7.66 mmol) was added dropwise over 10 minutes. The mixture was stirred at −78° C. for 1 hour, then 2-isopropoxy-4,4,5,5-tetramethyl-1,3,2-dioxaborolane (1.68 cm³ 8.22 mmol) was added rapidly to the solution. After an additional 1 hour at −78° C., the resulting mixture was warmed to room temperature and stirred overnight. The mixture was poured into water, extracted with diethyl ether four times and dried over magnesium sulfate. The solvent was removed under reduced pressure, and the residue was recrystallized two times in a methanol and acetone solution (ca. 3:1) to obtain the title product as a yellow crystalline solid (1.044 g, yield 44%). NMR (¹H, 300 MHz, CDCl₃): δ 8.99 (d, J=8.2 Hz, 2H); 8.69 (d, J=7.4 Hz, 2H); 8.47 (s, 2H); 7.87 (t, J=7.9 Hz, 2H), 4.78 (t, J=7.0 Hz, 2H); 2.13 (m, 2H); 1.50 (s, 24H); 1.39 (br, 4H); 1.25 (br, 6H); 0.85 (t, J=6.8 Hz, 3H).

Poly[2,7-N-octylphenanthro[1,10,9,8-c,d,e,f,g]carbazole-alt-5,5-(4',7'-di-2-thienyl-2',1',3'-benzothiadiazole)] 3

In a dried flask, 2,7-bis(4,4,5,5-tetramethyl-1,3,2-dioxaborolan-2-yl)-N-octylphenanthro[1,10,9,8-c,d,e,f,g]carbazole (500.0 mg, 0.7943 mmol), 4,7-di(2'-bromothien-5'-yl)-2,1,3-benzothiadiazole (567.7 mg, 0.7943 mmol), tris(dibenzylideneacetone)dipalladium(0) (3.6 mg, 0.0040 mmol), tri(o-tolyl)phosphine (4.9 mg, 0.0160 mmol) and Aliquat 336 (50 mg) were dissolved in degassed toluene (8.0 cm³) and degassed 2.0 M aqueous potassium carbonate (3.2 cm³). The reaction mixture was vigorously stirred at 100-105° C. for 24 hours. The polymer was purified by precipitation into methanol:water (10:1), filtered and washed sequentially via Soxhlet extraction with acetone, petroleum ether and chloroform. The chloroform fraction was reduced to a smaller volume under reduced pressure and precipitated into methanol (500 cm³). The precipitated polymer was filtered and dried under vacuum at 25° C. overnight to afford the title product 3 (674 mg, yield 91%). $M_n$=12,500 g/mol, $M_w$=30,000 g/mol. $\lambda_{max}$=563 nm (solid state), 536 nm (chlorobenzene).

Example 4

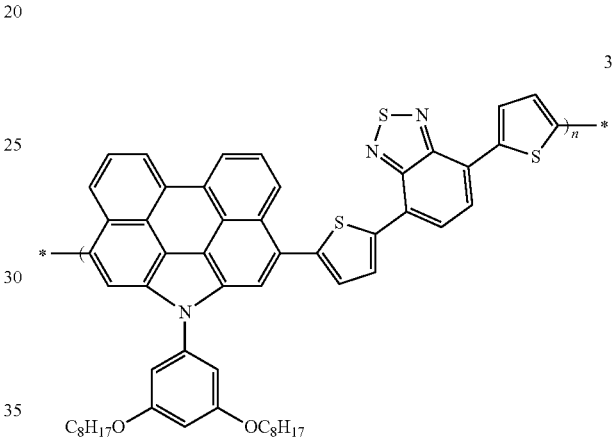

3

Poly[2,7-N-3',5'-bis(octyloxyphenyl)phenanthro[1,10,9,8-c,d,e,f,g]carbazole-alt-5,5'-(4',7'-di-2-thienyl-2',1',3'-benzothiadiazole)]-4 was prepared as described below 1-Iodo-3,5-dimethoxybenzene A dried round bottom flaks was charged with 1-bromo-3,5-dimethoxybenzene (15.0 g, 69.1 mmol) and dry tetrahydrofuran (275 cm³). The resulting solution was cooled down to −78° C., then n-butyllithium (2.5 M in hexanes, 29.0 cm³, 72.6 mmol) was added dropwise over 10 minutes. The mixture was stirred at −78° C. for 1 hour, then 1,2-iodoethane (20.5 g, 72.6 mmol) in dry tetrahydrofuran (75 cm³) was added rapidly to the solution. After an additional 1 hour at −78° C., the resulting mixture was warmed to room temperature and stirred overnight. The mixture was poured into saturated sodium thiosulfate solution (200 cm³), extracted with diethyl ether four times and dried over magnesium sulfate. The solvent was removed under reduced pressure, and the residue was recrystallized from methanol to obtain the title product as a white crystalline solid (13.0 g, yield 71%). NMR (¹H, 300 MHz, CDCl₃): δ 6.85 (d, J=2.3 Hz, 2H); 6.40 (t, J=2.3 Hz, 1H); 3.76 (s, 6H).

5-Iodobenzene-1,3-diol

A dried round bottom flaks was charged with 1-iodo-3,5-dimethoxy-benzene (21.7 g, 82.1 mmol) and dry dichloromethane (400 cm³). The resulting solution was cooled down to −78° C., then boron tribromide (19.8 cm³, 205 mmol) was added dropwise over 15 minutes. The mixture was stirred at −78° C. for 2 hours, and then the resulting mixture was warmed to 25° C. and stirred. After 18 hours, methanol (40 cm³) and dilute hydrochloric acid (110 cm³) were added very slowly and the aqueous layer washed three times with dichloromethane and then the aqueous layer was extracted three times with diethyl ether. The combined diethyl ether fractions were dried over magnesium sulfate and the solvent was removed under reduced pressure to obtain the title product as a colourless oil which crystallized into a white solid (17.6 g, yield 91%). NMR ($^1$H, 300 MHz, DMSO-$d_6$): δ 9.58 (s, 2H); 6.58 (d, J=2.1 Hz, 2H); 6.21 (t, J=2.1 Hz, 1H).

1-Iodo-3,5-bis-octyloxy-benzene

A dried flask fitted with a condenser was charged with 5-iodo-benzene-1,3-diol (10.1 g, 42.8 mmol), bromooctane (15.5 cm³, 89.9 mmol), potassium carbonate (29.6 g, 214 mmol) and acetonitrile (170 cm³). The resulting solution was reflux for 18 hours and then poured into distilled water (300 cm³). The resulting solution was extracted with petroleum ether (3×250 cm³). The combined organic fractions were dried over magnesium sulfate and the solvent was removed under reduced pressure. The crude product was dissolved in dichloromethane, pre-adsorbed on silica gel, purified by column chromatography (silica gel, 98:2, petroleum ether:ethyl acetate as eluent) to yield the title product as a colourless solid (17.3 g, yield 82%). NMR ($^1$H, 300 MHz, CDCl$_3$): δ 6.82 (d, J=2.2 Hz, 2H); 6.38 (t, J=2.2 Hz, 1H); 3.88 (t, J=6.6 Hz, 4H); 1.74 (m, 4H); 1.42 (br, 4H); 1.29 (br, 16H); 0.89 (t, J=6.8 Hz, 6H).

N-3',5'-Bis(octyloxyphenyl)phenanthro[1,10,9,8-c,d,e,f,g]carbazole

A dried flask fitted with a condenser was charged with N-hydro-phenanthro[1,10,9,8-c,d,e,f,g]carbazole (4.50 g, 17.0 mmol), 1-iodo-3,5-bis-octyloxy-benzene (9.76 g, 21.2 mmol), potassium carbonate (2.93 g, 21.2 mmol), copper powder (0.108 g, 1.70 mmol), 18-crown-6 (0.448 g, 1.70 mmol) and 1,2-dichlorobenzene (170 cm³). The resulting solution was reflux for 48 hours and then poured into 1 N hydrochloric acid (200 cm³). The resulting solution was extracted with dichloromethane (3×250 cm³). The combined organic fractions were dried over magnesium sulfate and the solvent was removed under reduced pressure. The crude product was dissolved in dichloromethane, pre-adsorbed on silica gel, purified by column chromatography (silica gel, 80:20, petroleum ether:dichloromethane as eluent). The resulting product was dissolved into a small tetrahydrofuran volume and precipitate in methanol resulting in the title product as a yellow solid (4.02 g, yield 39%). NMR ($^1$H, 300 MHz, CDCl$_3$): δ 8.63 (d, J=7.5 Hz, 2H); 8.10 (d, J=8.0 Hz, 2H); 7.99 (d, J=8.9 Hz, 2H); 7.91 (d, J=8.9 Hz, 2H); 7.81 (t, J=7.8 Hz, 2H); 7.00 (d, J=2.2 Hz, 2H); 6.55 (t, J=2.2 Hz, 1H); 4.06 (t, J=6.6 Hz, 4H); 1.85 (m, 4H); 1.51 (br, 4H); 1.30 (br, 16H); 0.89 (t, J=6.9 Hz, 6H).

2,7-Dibromo-N-3',5'-bis(octyloxyphenyl)phenanthro[1,10,9,8-c,d,e,f,g]carbazole

A dried round bottom flask was charged with N-3,5-bis(octyloxyphenyl)phenanthro[1,10,9,8-c,d,e,f,g]carbazole (3.80 g, 6.36 mmol) and dichloromethane (320 cm³). To this solution, N-bromosuccimide (2.26 g, 12.7 mmol) was added slowly. The solution was stirred for 60 minutes at 25° C. and then poured into distilled water (200 cm³). The solution was stirred for 120 minutes at 25° C. and then the solvent removed under vacuum. The crude product was pre-absorded on silica gel and purified by column chromatography (silica gel, 80:20, petroleum ether:dichloromethane as eluant) and recrystallized into tetrahydrofuran and methanol solution (ca. 1:3) to afford the title product as a yellow solid (4.24 g, yield 88%). NMR ($^1$H, 300 MHz, CDCl$_3$): δ 8.49 (d, J=7.5 Hz, 2H); 8.25 (d, J=8.3 Hz, 2H); 8.19 (s, 2H); 7.81 (t, J=7.9 Hz, 2H); 6.88 (d, J=2.2 Hz, 2H); 6.57 (t, J=2.2 Hz, 1H); 4.08 (t, J=6.6 Hz, 4H); 1.88 (m, 4H); 1.53 (br, 4H); 1.30 (br, 16H); 0.89 (t, J=6.9 Hz, 6H).

2,7-Bis(2-thienyl)-N-3',5'-bis(octyloxyphenyl)phenanthro[1,10,9,8-c,d,e,f,g]carbazole A dried round bottom flask fit with a condenser was charged with 2,7-dibromo-N-3',5'-bis(octyloxyphenyl)phenanthro[1,10,9,8-c,d,e,f,g]carbazole (4.10 g, 5.42 mmol), 2-(tributylstannyl)thiophene (3.88 cm³, 12.2 mmol), dichlorobis(triphenylphosphine)-palladium(II) (0.076 g, 0.109 mmol) and degassed toluene (55 cm³). The solution was stirred at reflux for 18 hours and then cold down. The reaction mixture was filtered over silica and eluted with petroleum ether. The solvent was removed under vacuum and the recovered solid triturated two times in methanol. The crude product was recrystallized into petroleum ether twice to afford the title product as a yellow solid (3.46 g, yield 84%)). NMR ($^1$H, 300 MHz, CDCl$_3$): δ 8.70 (d, J=7.5 Hz, 2H); 8.43 (d, J=8.3 Hz, 2H); 8.10 (s, 2H); 7.85 (t, J=7.9 Hz, 2H); 7.45 (m, 4H); 7.26 (t, J=2.2 Hz, 2H) 6.88 (d, J=2.2 Hz, 2H); 6.57 (t, J=2.2 Hz, 1H); 4.05 (t, J=6.6 Hz, 4H); 1.84 (m, 4H); 1.49 (br, 4H); 1.28 (br, 16H); 0.88 (t, J=6.9 Hz, 6H).

2,7-Bis(5-bromo-2-thienyl)-N-3',5'-bis(octyloxyphenyl)phenanthro[1,10,9,8-c,d,e,f,g]carbazole A dried round bottom flask was charged with 2,7-bis-(2-thienyl)-N-3',5'-bis(octyloxyphenyl)phenanthro[1,10,9,8-c,d,e,f,g]carbazole (1.50 g, 1.97 mmol) and dichloromethane (200 cm³). To this solution, N-bromosuccimide (0.718 g, 4.04 mmol) was added slowly. The solution was stirred for 24 hours at 25° C. and then poured into distilled water (200 cm³). The resulting solution was extracted with dichloromethane (2×100 cm³). The combined organic fractions were dried over magnesium sulfate, the solvent was removed under reduced pressure and the crude product recrystallized three times with petroleum ether (80-100° C.) to afford the title product as a yellow crystals (1.00 g, yield 55%). NMR ($^1$H, 300 MHz, CDCl$_3$): δ 8.70 (d, J=7.5 Hz, 2H); 8.41 (d, J=8.3 Hz, 2H); 8.02 (s, 2H); 7.87 (t, J=7.9 Hz, 2H); 7.20 (d, J=3.7 Hz, 2H); 7.18 (d, J=3.7 Hz, 2H) 6.95 (d, J=2.2 Hz, 2H); 6.56 (t, J=2.2 Hz, 1H); 4.06 (t, J=6.6 Hz, 4H); 1.86 (m, 4H); 1.50 (br, 4H); 1.28 (br, 16H); 0.88 (t, J=6.9 Hz, 6H).

Poly[2,7-N-3',5'-bis(octyloxyphenyl)phenanthro[1,10,9,8-c,d,e,f,g]carbazole-alt-5,5'-(4',7'-di-2-thienyl-2',1',3'-benzothiadiazole)]-4

In a dried flask, 2,7-bis(5-bromo-2-thienyl)-N-3',5'-bis(octyloxyphenyl)-phenanthro[1,10,9,8-c,d,e,f,g]carbazole (500.0 mg, 0.5436 mmol), 4,7-bis-(4,4,5,5-tetramethyl-[1,3,2]dioxaborolan-2-yl)-benzo[1,2,5]thiadiazole (2101.0 mg, 0.5436 mmol), tris(dibenzylideneacetone)dipalladium(0)

(2.5 mg, 0.0027 mmol), tri(o-tolyl)phosphine (3.3 mg, 0.0109 mmol) and Aliquat 336 (50 mg) were dissolved in degassed toluene (11.0 cm³) and degassed 2.0 M aqueous potassium carbonate (2.2 cm³). The reaction mixture was vigorously stirred at 100-105° C. for 21 hours. The polymer was purified by precipitation into methanol:water (10:1), filtered and washed sequentially via Soxhlet extraction with acetone, petroleum ether, chloroform and chlorobenzene. The chlorobenzene fraction was reduced to a smaller volume under reduced pressure and precipitated into methanol (500 cm³). The precipitated polymer was filtered and dried under vacuum at 25° C. overnight to afford the title product 4 (204 mg, yield 42%). $\lambda_{max}$=488 nm (solid state), 492 nm (chlorobenzene).

Example 5

Transistor Fabrication and Measurement

Thin-film organic field-effect transistors (OFETs) were fabricated on highly doped silicon substrates with thermally grown silicon oxide (SiO₂) insulating layer, where the substrate served as a common gate electrode. Transistor source-drain gold electrodes were photolithographically defined on the SiO₂ layer. Prior to organic semiconductor deposition, FET substrates were treated with octyltrichlorosilane (OTS). Thin semiconductor films were then deposited by spin-coating polymer solutions in dichlorobenzene (1 wt %) on FET substrates. The samples were then dried and annealed at 100° C. under nitrogen for 10 mins. The electrical characterization of the transistor devices was carried out in both dry nitrogen and ambient air atmosphere using computer controlled Agilent 4155C Semiconductor Parameter Analyser.

Transistor device characteristics for polymer 1 of Example 1 were measured on thin-films and the devices showed typical p-type behaviour with good current modulation, and well-defined linear and saturation regimes. For polymer 1, a charge carrier mobility in the saturation regime ($\mu_{sat}$) of $2 \times 10^{-4}$ cm²/Vs was calculated and a current on/off ratio of $1 \times 10^5$ was observed.

Field-effect mobility was calculated in the saturation regime ($V_d > (V_g - V_0)$) using equation (1):

$$dI_d^{sat}/dV_g = \mu_{sat} * (W * C_i / L) * (V_g - V_0) \quad (1)$$

where W is the channel width, L the channel length, $C_i$ capacitance of insulating layer, $V_g$ the gate voltage, $V_0$ the turn-on voltage, and $\mu_{sat}$ is the charge carrier mobility in the saturation regime. Turn-on voltage ($V_0$) was determined as the onset of source-drain current.

Example 6

Photovoltaic Cell Fabrication and Measurement

Organic photovoltaic (OPV) devices were fabricated on ITO-glass substrates (13 Ω/sq.) purchased from LUMTEC Corporation. Substrates were cleaned using common solvents (acetone, iso-propanol, deionized-water) in an ultrasonic bath prior to a conventional photolithography process that was carried out to define the bottom electrodes (anodes). A conducting polymer poly(ethylene dioxythiophene) doped with poly(styrene sulfonic acid) [Clevios VPAI 4083 (H. C. Starck)] was mixed in a 1:1 ratio with deionized-water. This solution was sonicated for 20 minutes to ensure proper mixing and filtered using a 0.2 μm filter before spin-coating to achieve a thickness of 20 nm. Substrates were exposed to ozone prior to the spin-coating process to ensure good wetting properties. Films were then annealed at 130° C. for 30 minutes in a nitrogen atmosphere where they were kept for the remainder of the process. Active materials solutions were prepared at the concentration and components ratio stated in the examples and stirred overnight. Thin films were either spin-coated or blade-coated in a nitrogen atmosphere to achieve active layer thicknesses between 100 and 200 nm as measured using a profilometer. A short drying period followed to ensure removal of any residual solvent. Typically, spin-coated films were dried at 23° C. for 10 minutes and blade-coated films were dried at 70° C. for 3 minutes on a hotplate. For the last step of the device fabrication, Ca (30 nm)/Al (200 nm) cathodes were thermally evaporated through a shadow mask to define the cells. Samples were measured at 23° C. under the irradiation of 1 Sun using a Solar Simulator (Newport Ltd, Model 91160) as the light source and using a calibrated Si-cell as the reference.

FIG. 1 illustrates the OPV device I-V characteristics, under irradiation of 1 Sun, for an OPV device prepared from polymer 1 of Example 1. The OPV device contains an active layer of the blend polymer 1:PCBM[C60] 1:3 blade-coated from a solution in DCB (23 mg/ml), with $V_{oc}$=830 mV
$J_{sc}$=9.75 mA/cm⁻²
FF=43.3%
η=3.50%

Power conversion efficiencies (η) of up to 3.50% were measured with an open-circuit voltage ($V_{OC}$) > 800 mV.

The invention claimed is:

1. A conjugated polymer comprising one or more identical or different repeating units of formula I

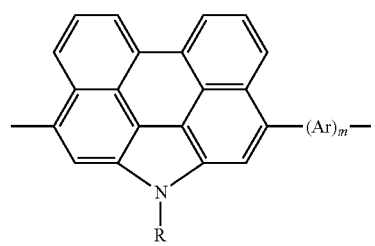

I wherein

R is on each occurrence identically or differently H, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR⁰=CR⁰⁰— or —C≡C— and in which one or more H atoms are optionally replaced by F, Cl, Br, I or CN, or R is an aryl, heteroaryl, aryloxy or heteroaryloxy group having 2 to 40 C atoms that is unsubstituted or substituted by one or more non-aromatic groups R¹, R⁰ and R⁰⁰ are independently of each other H or an optionally substituted carbyl or hydrocarbyl group optionally comprising one or more hetero atoms, Ar is on each occurrence identically or differently an optionally substituted aryl or heteroaryl group, —CY¹=CY²— or —C≡C—, Y¹ and Y² are independently of each other H, F, Cl or CN, R¹ is on each occurrence identically or differently H, halogen, —CN, —NC, —NCO, —NCS, —OCN, —SCN, —C(=O)NR⁰R⁰⁰, —C(=O)X⁰, —C(=O)R⁰, —NH₂, —NR⁰R⁰⁰, —SH, —SR⁰, —SO₃H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, P is a polymerisable group, Sp is a spacer group or a single bond, X$^0$ is halogen, m is on each occurrence identically or differently 0, 1, 2 or 3, and wherein the benzene rings are optionally substituted with one or more groups R$^1$.

2. A polymer according to claim 1, wherein formula I is selected from the group consisting of the following subformulae:

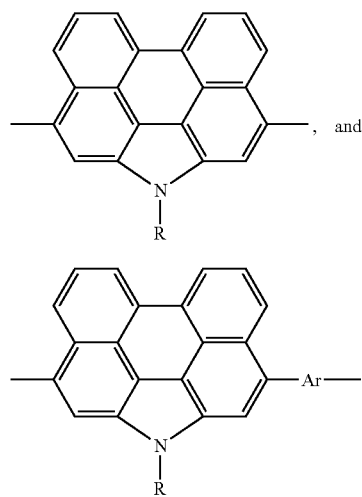

wherein

R is on each occurrence identically or differently H, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR$^0$=CR$^{00}$— or —C≡C— and in which one or more H atoms are optionally replaced by F, Cl, Br, I or CN, or R is an aryl, heteroaryl, aryloxy or heteroaryloxy group having 2 to 40 C atoms that is unsubstituted or substituted by one or more non-aromatic groups R$^1$, R$^0$ and R$^{00}$ are independently of each other H or an optionally substituted carbyl or hydrocarbyl group optionally comprising one or more hetero atoms, Ar is on each occurrence identically or differently an optionally substituted aryl or heteroaryl group, —CY$^1$=CY$^2$— or —C≡C—, Y$^1$ and Y$^2$ are independently of each other H, F, Cl or CN, R$^1$ is on each occurrence identically or differently H, halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$ optionally substituted silyl, carbyl or hydrocarbyl with 1 to 40 C atoms that is optionally substituted and optionally comprises one or more hetero atoms, or P-Sp-, P is a polymerisable group, Sp is a spacer group or a single bond, X$^0$ is halogen, and the benzene rings are optionally substituted with one or more groups R$^1$.

3. A polymer according to claim 1, which is of formula II

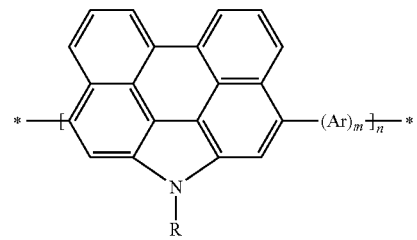

wherein

R is on each occurrence identically or differently H, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR$^0$=CR$^{00}$— or —C≡C— and in which one or more H atoms are optionally replaced by F, Cl, Br, I or CN, or R is an aryl, heteroaryl, aryloxy or heteroaryloxy group having 2 to 40 C atoms that is unsubstituted or substituted by one or more non-aromatic groups R$^1$, R$^0$ and R$^{00}$ are independently of each other H or an optionally substituted carbyl or hydrocarbyl group optionally comprising one or more hetero atoms, Ar is on each occurrence identically or differently an optionally substituted aryl or heteroaryl group, —CY$^1$=CY$^2$— or —C≡C—, Y$^1$ and Y$^2$ are independently of each other H, F, Cl or CN, R$^1$ is on each occurrence identically or differently H, halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, P is a polymerisable group, Sp is a spacer group or a single bond, X$^0$ is halogen, m is on each occurrence identically or differently 0, 1, 2 or 3, the benzene rings are optionally substituted with one or more groups R$^1$, and n is an integer >1.

4. A polymer according to claim 3, selected from the group consisting of the following formulae

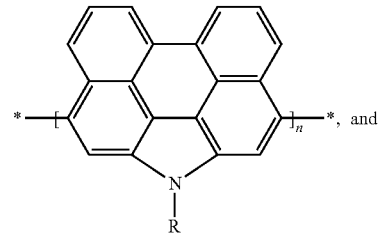

-continued

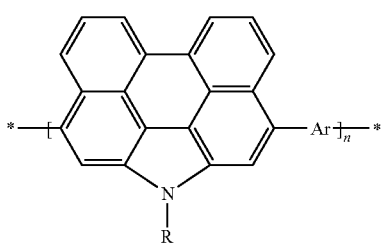

II2 wherein

R is on each occurrence identically or differently H, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR$^0$=CR$^{00}$— or —C≡C— and in which one or more H atoms are optionally replaced by F, Cl, Br, I or CN, or R is an aryl, heteroaryl, aryloxy or heteroaryloxy group having 2 to 40 C atoms that is unsubstituted or substituted by one or more non-aromatic groups R$^1$, R$^0$ and R$^{00}$ are independently of each other H or an optionally substituted carbyl or hydrocarbyl group optionally comprising one or more hetero atoms, Ar is on each occurrence identically or differently an optionally substituted aryl or heteroaryl group, —CY$^1$=CY$^2$— or —C≡C—, Y$^1$ and Y$^2$ are independently of each other H, F, Cl or CN, R$^1$ is on each occurrence identically or differently H, halogen, —CN, —NC, —NCO, —NCS, —OCN, —SCN, —C(=O)NR$^0$R$^{00}$, —C(=)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, P is a polymerisable group, Sp is a spacer group or a single bond, X$^0$ is halogen, and n is an integer >1.

5. A polymer according to claim 3, which is of formula IIa

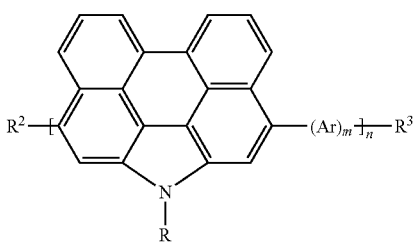

IIa wherein

R is on each occurrence identically or differently H, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR$^0$=CR$^{00}$— or —C≡C— and in which one or more H atoms are optionally replaced by F, Cl, Br, I or CN, or R is an aryl, heteroaryl, aryloxy or heteroaryloxy group having 2 to 40 C atoms that is unsubstituted or substituted by one or more non-aromatic groups R$^1$, R$^0$ and R$^{00}$ are independently of each other H or an optionally substituted carbyl or hydrocarbyl group optionally comprising one or more hetero atoms, Ar is on each occurrence identically or differently an optionally substituted aryl or heteroaryl group, —CY$^1$=CY$^2$— or —C≡C—, Y$^1$ and Y$^2$ are independently of each other H, F, Cl or CN, R$^1$ is on each occurrence identically or differently H, halogen, —CN, —NC, —NCO, —NCS, —OCN, —SCN, —C(=O)NR$^0$R$^{00}$, —C(=)X$^0$, —C(=O) R$^0$—NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, P is a polymerisable group, Sp is a spacer group or a single bond, X$^0$ is halogen, m is on each occurrence identically or differently 0, 1, 2 or 3, and n is an integer >1 the benzene rings are optionally substituted with one or more groups R$^1$, and

R$^2$ and R$^3$ have independently of each other one of the meanings of R$^1$, or denote —CH$_2$Cl, —CHO, —CH=CH$_2$, —SiR'R"R'", —SnR'R"R'", —BR'R", —B(OR')(OR"), —B(OH)$_2$, or P-Sp, P is a polymerisable group, Sp is a spacer group or a single bond, R'" has one of the meanings of R$^0$, R' and R" have independently of each other one of the meanings of R$^0$, or form a ring together with the hetero atom to which they are attached, and R$^0$ is H or an optionally substituted carbyl or hydrocarbyl group optionally comprising one or more hetero atoms.

6. A polymer according to claim 3, which is of formula IIa1

R$^2$-chain-R$^3$      IIa1 wherein

R$^2$ and R$^3$ have independently of each other one of the meanings of R$^1$, or denote —CH$_2$Cl, —CHO, —CH=CH$_2$, —SiR'R"R'", —SnR'R"R'", —BR'R", —B(OR')(OR"), —B(OH)$_2$, or P-Sp, P is a polymerisable group, Sp is a spacer group or a single bond, and R', R" and R'" have independently of each other one of the meanings of R$^0$ and R' and R" may also form a ring together with the hetero atom to which they are attached, R$^0$ is H or an optionally substituted carbyl or hydrocarbyl group optionally comprising one or more hetero atoms, and "chain" is a polymer chain selected from the group consisting of formulae II1 and II2

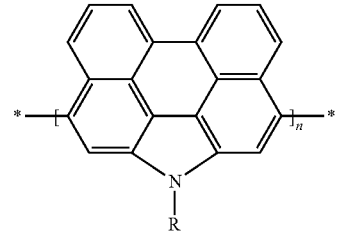

II1

-continued

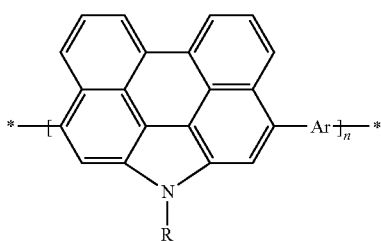

II2 wherein
R is on each occurrence identically or differently H, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR$^o$=CR$^{oo}$— or —C≡C— and in which one or more H atoms are optionally replaced by F, Cl, Br, I or CN, or R is an aryl, heteroaryl, aryloxy or heteroaryloxy group having 2 to 40 C atoms that is unsubstituted or substituted by one or more non-aromatic groups R$^1$,
R$^o$ and R$^{oo}$ are independently of each other H or an optionally substituted carbyl or hydrocarbyl group optionally comprising one or more hetero atoms,
Ar is on each occurrence identically or differently an optionally substituted aryl or heteroaryl group, —CY$^1$=CY$^2$— or —C≡C—,
Y$^1$ and Y$^2$ are independently of each other H, F, Cl or CN,
R$^1$ is on each occurrence identically or differently H, halogen, —CN, —NC, —NCO, —NCS, —OCN, —SCN, —C(=O)NR$^o$R$^{oo}$, —C(=)X$^o$, —C(=O)R$^o$, —NH$_2$, —NR$^o$R$^{oo}$, —SH, —SR$^o$, —SO$_3$H, —SO$_2$R$^o$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-,
P is a polymerisable group,
Sp is a spacer group or a single bond,
X$^o$ is halogen, and
n is an integer >1.

7. A polymer according to claim 1, wherein Ar is selected from the group consisting of benzo[1,2,3]thiadiazole-4,7-diyl, benzo[1,2,3]selenadiazole-4,7-diyl, benzo[1,2,5]thiadiazole-4,7,diyl, benzo[1,2,5]selenadiazole-4,7,diyl, 4,7-di-thien-2-yl-benzo[1,2,3]thiadiazole, 4,7-di-thien-2-yl-benzo[1,2,5]thiadiazole, 2,3-dicyano-1,4-phenylene, 2,5-dicyano, 1,4-phenylene, 2,3-difluro-1,4-phenylene, 2,5-difluoro,1,4-phenylene, 2,3,5,6-tetrafluoro,1,4-phenylene, 3,4-difluorothiophene-2,5-diyl, thieno[3,4-b]pyrazine-2,5-diyl, quinoxaline-5,8-diyl, selenophene-2,5-diyl, thiophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, 1,4-phenylene, pyridine-2,5-diyl, pyrimidine-2,5-diyl, p-p'-biphenyl, naphthalene-2,6-diyl, benzo[1,2-b:4,5-b]dithiophene-2,6-diyl, 2,2-dithiophene, 2,2-diselenophene, thiazole, and oxazole, all of which are unsubstituted, mono- or polysubstituted with R$^1$, wherein
R$^1$ is on each occurrence identically or differently H, halogen, —CN, —NC, —NCO, —NCS, —OCN, —SCN, —C(=O)NR$^o$R$^{oo}$, —C(=)X$^o$, —C(=O)R$^o$, —NH$_2$, —NR$^o$R$^{oo}$, —SH, —SR$^o$, —SO$_3$H, —SO$_2$R$^o$, —OH, —NO$_2$, —CF$_3$, —SF$_5$, optionally substituted silyl carbyl or hydrocarbyl with 1 to 40 C atoms that is optionally substituted and optionally comprises one or more hetero atoms, or P-Sp-,
P is a polymerisable group,
Sp is a spacer group or a single bond,
X$^o$ is halogen, and
R$^o$ and R$^{oo}$ are independently of each other H or an optionally substituted carbyl or hydrocarbyl group optionally comprising one or more hetero atoms.

8. A polymer according to claim 1, wherein R is selected from the group consisting of the following formulae

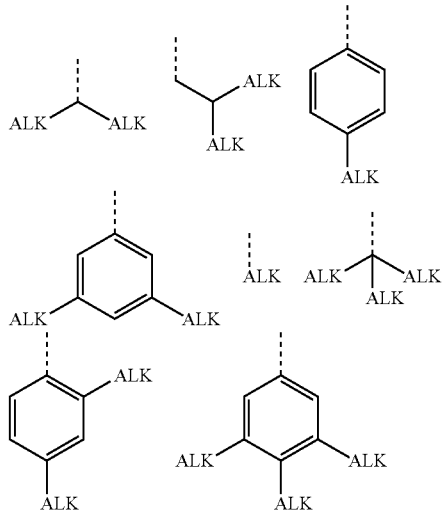

wherein "ALK" denotes optionally fluorinated, optionally linear, alkyl or alkoxy with 1 to 20 C-atoms, and the dashed line denotes the link to the N-atom of the phenanthrocarbazole core in formula I, and optionally all ALK subgroups are identical.

9. A polymer according to claim 1, wherein R is primary alkyl or alkoxy with 1 to 30 C atoms, secondary alkyl or alkoxy with 3 to 30 C atoms, tertiary alkyl or alkoxy with 4 to 30 C atoms, wherein in all these groups one or more H atoms are optionally replaced by F, or R is selected from aryl, alkylated aryl or alkoxy aryl with 4 to 40 C atoms.

10. A formulation comprising one or more polymers according to claim 1 and one or more solvents, optionally selected from organic solvents.

11. A charge transport, semiconducting, electrically conducting, photoconducting or light emitting material in optical, electrooptical, electronic, electroluminescent or photoluminescent component or device, comprising a polymer according to claim 1.

12. An optical, electrooptical or electronic component or device comprising one or more polymers according to claim 1.

13. A component or device according to claim 12, which is selected from the group consisting of organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), Schottky diodes, planarising layers, antistatic films, polymer electrolyte membranes (PEM), conducting substrates, conducting patterns, electrode materials in batteries, alignment layers, biosensors, biochips, security markings, security devices, and components and devices for detecting and discriminating DNA sequences.

14. A process of preparing a polymer according to claim 1, comprising coupling one or more monomers of formula III

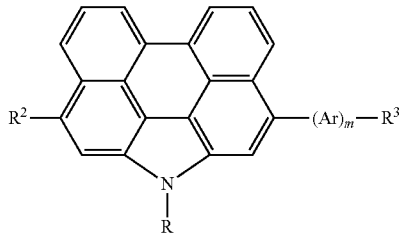

wherein
R is on each occurrence identically or differently H, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR$^0$=CR$^{00}$— or —C≡C— and in which one or more H atoms are optionally replaced by F, Cl, Br, I or CN, or R is an aryl, heteroaryl, aryloxy or heteroaryloxy group having 2 to 40 C atoms that is unsubstituted or substituted by one or more non-aromatic groups R$^1$, R$^0$ and R$^{00}$ are independently of each other H or an optionally substituted carbyl or hydrocarbyl group optionally comprising one or more hetero atoms, Ar is on each occurrence identically or differently an optionally substituted aryl or heteroaryl group, —CY$^1$=CY$^2$— or —C≡C—, Y$^1$ and Y$^2$ are independently of each other H, F, Cl or CN, R$^1$ is on each occurrence identically or differently H, halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, P is a polymerisable group,
Sp is a spacer group or a single bond,
X$^0$ is halogen,
m is on each occurrence identically or differently 0, 1, 2 or 3, R$^2$ and R$^3$ have independently of each other one of the meanings of R$^1$, or denote —CH$_2$Cl, —CHO, —CH=CH$_2$, —SiR'R"R'", —SnR'R"R'", —BR'R", —B(OR')(OR"), —B(OH)$_2$, or P-Sp, and R', R" and R'" have independently of each other one of the meanings of R$^0$ and R' and R" may also form a ring together with the hetero atom to which they are attached, and the benzene rings are optionally substituted with one or more groups R$^1$, with each other, and/or with one or more monomers of the formula R$^2$—Ar—R$^3$, wherein R$^2$, R$^3$ and Ar are as defined for the compound of formula III in an aryl-aryl coupling reaction.

15. A process according to claim 14, wherein in the monomer of formula III R is on each occurrence identically or differently H, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR$^0$=CR$^{00}$— or —C≡C— and in which one or more H atoms are optionally replaced by F, Cl, Br, I or CN, or R is an aryl, heteroaryl, aryloxy or heteroaryloxy group having 2 to 40 C atoms that is unsubstituted or substituted by one or more non-aromatic groups R$^1$, R$^0$ and R$^{00}$ are independently of each other H or a carbyl or hydrocarbyl group optionally comprising one or more hetero atoms, Ar is on each occurrence identically or differently an aryl or heteroaryl group, —CY$^1$=CY$^2$— or —C≡C—, Y$^1$ and Y$^2$ are independently of each other H, F, Cl or CN, R$^1$ is on each occurrence identically or differently H, halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, silyl, carbyl or hydrocarbyl with 1 to 40 C atoms and optionally comprises one or more hetero atoms, or P-Sp-, P is a polymerisable group,
Sp is a spacer group or a single bond,
X$^0$ is halogen,
m is on each occurrence identically or differently 0, 1, 2 or 3, R$^2$ and R$^3$ have independently of each other one of the meanings of R$^1$, or denote —CH$_2$Cl, —CHO, —CH=CH$_2$, —SiR'R"R'", —SnR'R"R'", —BR'R", —B(OR')(OR"), —B(OH)$_2$, or P-Sp, and R', R" and R'" have independently of each other one of the meanings of R$^0$ and R' and R" may also form a ring together with the hetero atom to which they are attached, and the benzene rings are optionally substituted with one or more groups R$^1$.

16. A process according to claim 14, wherein the monomer of formula III is selected from the following formulae:

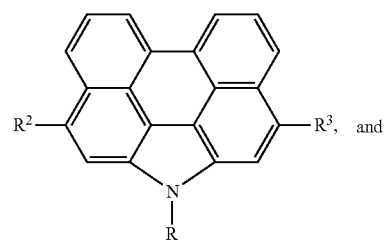

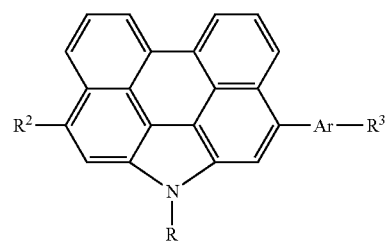

wherein R, R$^2$ and R$^3$ and Ar have the meanings given for formula III, and the benzene rings are optionally substituted with one or more groups R$^1$, wherein R¹ is on each occurrence identically or differently H, halogen, —CN, —NC, —NCO, —NCS, —OCN, —SCN, —C(=O)NR⁰R⁰⁰, —C(=)X⁰, —C(=O)R⁰, —NH₂, —NR⁰R⁰⁰, —SH, —SR⁰, —SO₃H, —SO₂R⁰, —OH, —NO₂, —CF₃, —SF₅, silyl, carbyl, or hydrocarbyl with 1 to 40 C atoms and optionally comprises one or more hetero atoms, or P—Sp-, P is a polymerisable group,
Sp is a spacer group or a single bond,
X⁰ is halogen, and
R⁰ and R⁰⁰ are independently of each other H or a carbyl or hydrocarbyl group optionally comprising one or more hetero atoms.

17. A process according to claim 14, wherein in the monomer of formula III, Ar is selected from the group consisting of benzo[1,2,3]thiadiazole-4,7-diyl, benzo[1,2,3]selenadiazole-4,7-diyl, benzo[1,2,5]thiadiazole-4,7,diyl, benzo[1,2,5]selenadiazole-4,7,diyl, 4,7-di-thien-2-yl-benzo[1,2,3]thiadiazole, 4,7-di-thien-2-yl-benzo[1,2,5]thiadiazole, 2,3-dicyano-1,4-phenylene, 2,5-dicyano,1,4-phenylene, 2,3-difluoro-1,4-phenylene, 2,5-difluoro,1,4-phenylene, 2,3,5,6-tetrafluoro,1,4-phenylene, 3,4-difluorothiophene-2,5-diyl, thieno[3,4-b]pyrazine-2,5-diyl, quinoxaline-5,8-diyl, selenophene-2,5-diyl, thiophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, 1,4-phenylene, pyridine-2,5-diyl, pyrimidine-2,5-diyl, p-p'-biphenyl, naphthalene-2,6-diyl, benzo[1,2-b:4,5-b']dithiophene-2,6-diyl, 2,2-dithiophene, 2,2-diselenophene, thiazole, and oxazole, all of which are unsubstituted, mono- or polysubstituted with R¹, wherein R¹ is on each occurrence identically or differently H, halogen, —CN, —NC, —NCO, —NCS, —OCN, —SCN, —C(=O)NR⁰R⁰⁰, —C(=)X⁰, —C(=O)R⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms, or P-Sp-, P is a polymerisable group,
Sp is a spacer group or a single bond,
X⁰ is halogen, and
R⁰ and R⁰⁰ are independently of each other H or an optionally substituted carbyl or hydrocarbyl group optionally comprising one or more hetero atoms.

18. A process according to claim 14, wherein in the monomer of formula III, R is selected from the group consisting of the following formulae

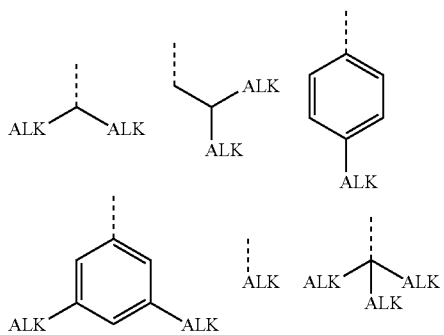
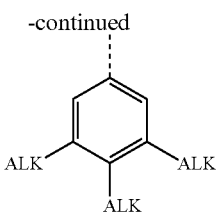

-continued

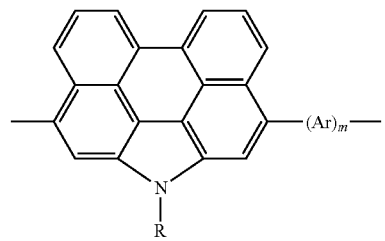

wherein "ALK" denotes optionally fluorinated, optionally linear, alkyl or alkoxy with 1 to 20 C-atoms, and the dashed line denotes the link to the N-atom of the phenanthrocarbazole core in formula I, and optionally all ALK subgroups are identical.

19. A process according to claim 14, wherein in the monomer of formula III, R is primary alkyl or alkoxy with 1 to 30 C atoms, secondary alkyl or alkoxy with 3 to 30 C atoms, tertiary alkyl or alkoxy with 4 to 30 C atoms, wherein in all these groups one or more H atoms are optionally replaced by F, or R is selected from aryl, alkylated aryl or alkoxy aryl with 4 to 40 C atoms.

20. A mixture or blend comprising one or more compounds or polymers selected from the group consisting of compounds and polymers having semiconducting, charge transport, hole/electron transport, hole/electron blocking, electrically conducting, photoconducting or light emitting properties and a conjugated polymer comprising one or more identical or different repeating units of formula I

I wherein
R is on each occurrence identically or differently H, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR⁰=CR⁰⁰— or —C≡C— and in which one or more H atoms are optionally replaced by F, Cl, Br, I or CN, or R is an aryl, heteroaryl, aryloxy or heteroaryloxy group having 2 to 40 C atoms that is unsubstituted or substituted by one or more non-aromatic groups R¹, R⁰ and R⁰⁰ are independently of each other H or an optionally substituted carbyl or hydrocarbyl group optionally comprising one or more hetero atoms, Ar is on each occurrence identically or differently an optionally substituted aryl or heteroaryl group, —CY¹=CY²— or —C≡C—, Y¹ and Y² are independently of each other H, F, Cl or CN, R¹ is on each occurrence identically or differently H, halogen, —CN, —NC, —NCO, —NCS, —OCN, —SCN, —C(=O)NR⁰R⁰⁰, —C(=O)X⁰, —C(=O)R⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms, or P-Sp-, P is a polymerisable group, Sp is a spacer group or a single bond, $X^0$ is halogen, m is on each occurrence identically or differently 0, 1, 2 or 3, and wherein the benzene rings are optionally substituted with one or more groups $R^1$.

21. An optical, electrooptical or electronic component or device, which is an OFET device or a bulk heterojunction OPV device, which comprises a conjugated polymer comprising one or more identical or different repeating units of formula I

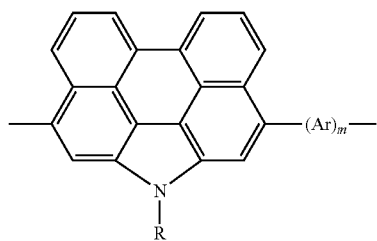

I wherein

R is on each occurrence identically or differently H, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR$^0$=CR$^{00}$— or —C≡C— and in which one or more H atoms are optionally replaced by F, Cl, Br, I or CN, or R is an aryl, heteroaryl, aryloxy or heteroaryloxy group having 2 to 40 C atoms that is unsubstituted or substituted by one or more non-aromatic groups $R^1$, $R^0$ and $R^{00}$ are independently of each other H or an optionally substituted carbyl or hydrocarbyl group optionally comprising one or more hetero atoms, Ar is on each occurrence identically or differently an optionally substituted aryl or heteroaryl group, —CY$^1$=CY$^2$— or —C≡C—, $Y^1$ and $Y^2$ are independently of each other H, F, Cl or CN, $R^1$ is on each occurrence identically or differently H, halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, P is a polymerisable group, Sp is a spacer group or a single bond, $X^0$ is halogen, m is on each occurrence identically or differently 0, 1, 2 or 3, and wherein the benzene rings are optionally substituted with one or more groups $R^1$.

* * * * *